(12) United States Patent
Song et al.

(10) Patent No.: US 11,954,873 B1
(45) Date of Patent: Apr. 9, 2024

(54) ARTIFICIAL INTELLIGENCE-BASED DEVICES AND METHODS FOR GEOMETRIC ALIGNMENT AND PREPROCESSING OF RAW CT IMAGES

(71) Applicant: Heuron Co., Ltd., Incheon (KR)

(72) Inventors: Ji Woo Song, Incheon (KR); Dohyun Kim, Suwon-si (KR); Soohwa Song, Incheon (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 18/367,804

(22) Filed: Sep. 13, 2023

(30) Foreign Application Priority Data

Mar. 30, 2023 (KR) ........................ 10-2023-0042266

(51) Int. Cl.
| | |
|---|---|
| *G06T 7/33* | (2017.01) |
| *A61B 6/00* | (2006.01) |
| *G06T 3/18* | (2024.01) |
| *G06T 3/40* | (2006.01) |
| *G06T 5/10* | (2006.01) |
| *G06T 7/00* | (2017.01) |
| *G06T 7/11* | (2017.01) |
| *G16H 30/40* | (2018.01) |

(52) U.S. Cl.
CPC ............ *G06T 7/337* (2017.01); *A61B 6/5205* (2013.01); *G06T 3/18* (2024.01); *G06T 3/40* (2013.01); *G06T 5/10* (2013.01); *G06T 7/0014* (2013.01); *G06T 7/11* (2017.01); *G16H 30/40* (2018.01); *G06T 2207/10081* (2013.01); *G06T 2207/20132* (2013.01); *G06T 2207/30008* (2013.01); *G06T 2207/30016* (2013.01); *G06T 2207/30101* (2013.01)

(58) Field of Classification Search
CPC .. G06T 15/00; G06T 1/00; G06T 3/00; G06T 2201/00; G06N 20/00; G06N 3/08; G06N 3/049
See application file for complete search history.

(56) References Cited

U.S. PATENT DOCUMENTS 11,263,749 B1 * 3/2022 Purushottam .......... G16H 15/00

FOREIGN PATENT DOCUMENTS

| KR | 10-2014-0096919 A | 8/2014 |
|---|---|---|
| KR | 10-1540254 B1 | 7/2015 |
| KR | 10-2016-0087784 A | 7/2016 |
| KR | 10-1754291 B1 | 7/2017 |

(Continued)

OTHER PUBLICATIONS

Helen Hong, et al., "Automatic vessel extraction by patient motion correction and bone removal in brain CT angiography", International Congress Series, 2005, vol. 1281, pp. 369-374.

(Continued)

*Primary Examiner* — Manuchehr Rahmjoo
(74) *Attorney, Agent, or Firm* — Sughrue Mion, PLLC

(57) ABSTRACT

The present disclosure relates to artificial intelligence-based devices and methods for geometric alignment and preprocessing of raw CT images. According to the present disclosure, when sensitive to a local error according to each characteristic, only linear transformation is applied to use the centrally aligned rigid registration result, and when the region of interest between patients is spatially matched or monitoring is required, a non-rigid registration result may be used.

11 Claims, 17 Drawing Sheets

(56) References Cited

FOREIGN PATENT DOCUMENTS

| | | | |
|---|---|---|---|
| KR | 10-1860566 | B1 | 5/2018 |
| KR | 10-1992057 | B1 | 6/2019 |
| KR | 10-2058884 | B1 | 12/2019 |
| KR | 10-2068836 | B1 | 2/2020 |

OTHER PUBLICATIONS

Korean Patent Office, Communication dated Jun. 20, 2023 in copending Korean Application No. 10-2023-0042266, with full English translation.
Korean Patent Office, Communication dated Sep. 27, 2023 in copending Korean Application No. 10-2023-0042266, with full English translation.

\* cited by examiner (a) EXAMPLE OF RIGID
TRANSFORMATION
(20)

(b) EXAMPLE OF NON-RIGID
TRANSFORMATION
(30)

ARTIFICIAL INTELLIGENCE-BASED DEVICES AND METHODS FOR GEOMETRIC ALIGNMENT AND PREPROCESSING OF RAW CT IMAGES

CROSS-REFERENCE TO RELATED APPLICATIONS

This application claims the priority of Korean Patent Application No. 10-2023-0042266 filed on Mar. 30, 2023, in the Korean Intellectual Property Office, the disclosure of which is incorporated herein by reference.

BACKGROUND

Field

The present disclosure relates to artificial intelligence-based devices and methods for geometric alignment and preprocessing of raw CT images. More specifically, the present disclosure relates to a device and a method capable of minimizing diversity caused by the size and shape, imaging direction, etc. of the patient's skull by applying a process of transforming any raw CT image in a consistent direction and size when the raw CT image has been input.

Description of the Related Art

Computed tomography is imaging by projecting thin X-rays around a cross section of the human body with X-rays, and measuring the amount to be reduced while these X-rays pass through the human body.

Since there is a slight difference in density of organs such as the kidneys, the degree of absorption varies depending on a direction in which X-rays are projected, and thus the human organs may be imaged through this test.

There are many types of computed tomography, and there is general tomography such as single slice CT, helical CT, and multi-slice CT (MSCT). The single slice CT is a computed tomography method capable of taking one picture from one rotation.

In the case of the helical CT, the images are taken while rotating X-rays in a spiral shape around the human body, and in the existing single slice CT, it is impossible to take a gap between two layers, but the helical CT performs the imaging without gaps, and thus there are advantages of obtaining more detailed images and acquiring a full-length picture quickly.

In the case of the multi-slice CT, X-ray projection may be performed quickly in a conical shape, and 64 individual images may be taken from one rotation.

Electron beam tomography (EBT) is a specific form of CT in which an X-ray tube having a sufficient size is configured to use and rotate a deflecting coil in a path of electrons moving between a cathode and an anode of the X-ray tube.

In the computed tomography, while the X-ray tube and a detector are connected to each other, the X-ray tube and the detector move left and right and rotate while moving an angle, and the X-rays are emitted in a straight line, and X-rays emitted through radar electromagnetic waves emitted into the air are collected in a conical shape.

The acquired data is processed using a tomographic reconstruction method that generates a series of cross-sectional images, and pixels of the image (two-dimensional units based on the size of a matrix and the field of view) are expressed in units of relative luminance.

In general, in order to derive stable performance from a deep learning model, an object is to minimize a gap between a learning data distribution and a test data distribution.

To this end, in a learning step, the diversity of train data is augmented and learned, and in a test step, standardized and generalized data are inferred.

A protocol taken for CT images varies greatly depending on a tomographer, a manufacturer, a situation, and a department in charge.

When the protocol is different even for the same patient, a geometric pattern of a taken 3D image is different, so that the images shown in 2D axial, coronal, and sagittal cross sections may look different.

Images taken with different protocols each time may be a factor in reducing the diagnostic accuracy from human/deep learning models.

In other words, in a series of processes of taking CT angiography in medical data, since protocols such as an imaging angle, an imaging area, a patient orientation, a slice thickness, a slice interval, etc. vary for each situation depending on a vendor of each hospital and habits of the tomographer, data has a problem of having geometrically various variances.

As a representative example, a Hounsfield Unit (HU) value may not be constant.

The pixel values have values of −1024 as a small value and 3071 as a large value, which are called the CT number, and the CT number is an equation consisting of a linear absorption coefficient of a material, an expansion constant, and a linear absorption coefficient of water, and this number is a fixed value, and the bone has a value of 1000 or more, water has a value of 0, air has a value of −1000, and the like, so that there is listed a table of which values of CT numbers have depending on a material. This number uses a unit called Hounsfield unit (HU), named after Hounsfield, which commercialized CT.

The CT number may be calculated by subtracting the linear absorption coefficient of water from the linear absorption coefficient of the material, multiplying by the expansion constant, and dividing the linear absorption coefficient of water. The Hounsfield unit (HU) is a standardized value representing CT images, and values defined as 0 HU for water and −1000 HU for air at standard temperature and pressure.

However, when comparing images taken in actual clinical practice, there is a problem in that the HU value of a specimen is not constant due to various factors, such as imaging equipment, a model, a temperature, a pressure, and imaging protocols (scan energy, radiation dose, etc.) set for each organ.

In addition, when low-dose CT images are applied to patients in consideration of radiation exposure and the like, the radiation scan amount set in the imaging protocol is low, and accordingly, there is a problem in that a lot of noise is synthesized in the CT image.

Accordingly, there is an emerging demand for technology development in devices and methods capable of minimizing diversity caused by the size and shape, imaging direction, etc. of the patient's skull by applying a process of transforming any raw CT image in a consistent direction and size when the raw CT image has been input.

RELATED ART DOCUMENT

Patent Document

1. Korean Patent Registration No. 10-1992057 (issued on Jun. 24, 2019)
2. Korean Patent Registration No. 10-1754291 (issued on Jul. 6, 2017)

SUMMARY

An object of the present disclosure is to provide artificial intelligence-based devices and methods for geometric alignment and preprocessing of raw CT images.

More specifically, the present disclosure is to provide a user with a device and a method capable of minimizing diversity caused by the size and shape, imaging direction, etc. of the patient's skull by applying a process of transforming any raw CT image in a consistent direction and size when the raw CT image has been input.

Meanwhile, the technical objects to be achieved in the present disclosure are not limited to the aforementioned technical objects, and other technical objects, which are not mentioned above, will be apparently understood to a person having ordinary skill in the art from the following description.

An aspect of the present disclosure provides an information providing method including: a first step of receiving a CT image by a head segmentation unit; a second step of predicting, by the head segmentation unit, a bone mask of the skull, a brain mask of the brain, and a brain-related vessel mask by passing the CT image through a head segmentation network capable of separating the skull and the brain; a third step of extracting, by the head segmentation unit, a brain image including only a brain region from the CT image by combining the predicted brain mask and vessel mask; a fourth step of receiving, by a rigid registration unit, standardized template data from an atlas unit and receiving a brain image from the head segmentation unit by fusing the characteristics of specific samples to be used as a reference for aligning a plurality of data into a common space; a fifth step of performing, by the rigid registration unit, rigid registration and affine registration between the template data and the brain image to acquire a transformation parameter; a sixth step of applying, by the rigid registration unit, rigid warping to the brain image based on the transformation parameter to acquire a first aligned brain image aligned by linear transformation; a seventh step of extracting, by a non-rigid registration unit, a deformation field which is a translation vector for each 3D voxel by inputting a 3D volume of the template data and a 3D volume of the first aligned brain image to a pre-learned non-rigid registration network; an eighth step of acquiring, by the non-rigid registration unit, a second aligned brain image more accurately registered to the actual brain than a result of the sixth step by performing non-rigid warping that applies grid interpolation in units of voxels to the first aligned brain image based on the deformation field; a ninth step of extracting, by a neurovascular segmentation unit, a cerebrovascular map from the second aligned brain image by passing the second aligned brain image through the neurovascular anatomy segmentation network; and a tenth step of providing, by a determination unit, brain-related information based on the cerebrovascular map.

The second step may include a 2-1 step of performing pre-processing which is at least one of a resizing operation, a HU windowing operation, and a normalizing operation with respect to the CT image; a 2-2 step of passing the pre-processed CT image through the head segmentation network; a 2-3 step of performing post-processing, which is at least one of a brain VOI crop operation and an outlier cluster removing operation with respect to the CT image passing through the head segmentation network; and a 2-4 step of predicting the bone mask, the brain mask, and the vessel mask based on the post-processed CT image.

In the 2-1 step, the resizing operation may be an operation of reducing and/or enlarging an image to a size required by the head segmentation network, the HU windowing operation may be an operation of setting the upper and lower limits of a Hounsfield unit (HU), and the normalizing operation may be an operation of determining a HU Level from the set lower limit to the upper limit, and mapping the HU level at a determined [0, 1] interval, and in the 2-3 step, the brain VOI crop operation may be an operation of resizing after removing a region other than a volume region of interest for the brain, and the outlier cluster removing operation may be an operation of removing the outlier cluster that is not connected but separated on three dimensions.

The standardized template data of the atlas unit may be generated by aligning the specific sample data in the center so that anatomical patterns or characteristics are preserved and synthesizing the specific sample data after non-rigid registration according to a predetermined level.

Rigid warping based on the transformation parameter may apply linear transformations including translation, rotation, and scale transformations so that the brain image may be deformed while maintaining an original ratio without distortion.

In the non-rigid warping based on the deformation field, the alignment may be performed to make a shape more consistent with the actual brain by performing detailed secondary alignment on the first aligned brain image based on the transformation parameter by applying the grid interpolation in units of voxels.

In the sixth step, first aligned bone mask, brain mask, and vessel mask aligned in a linear transformation may be acquired by applying the rigid warping to the bone mask, the brain mask, and the vessel mask based on the transformation parameter, in the eighth step, second aligned bone mask, brain mask, and vessel mask may be acquired by applying non-rigid warping of applying grid interpolation in units of voxels based on the deformation field to the first aligned bone mask, brain mask, and vessel mask, and in the tenth step, the determination unit may provide the information by further using at least one of the second aligned bone mask, brain mask, and vessel mask based on the cerebrovascular map.

After the tenth step, the second aligned brain image, and the second aligned bone mask, brain mask, and vessel mask may restore/inversely transform the first aligned brain image and the first aligned bone mask, brain mask, and vessel mask into a space of the original raw CT image by inversely transforming and applying the deformation field, and the first aligned brain image and the first aligned bone mask, brain mask, and vessel mask may restore/inversely transform the brain image, the bone mask, the brain mask, and the vessel mask into a space of the original raw CT image by inversely transforming and applying the transformation parameter.

The ninth step may include a 9-1 step of performing pre-processing, which is at least one of a HU windowing operation, a normalizing operation, and a patch sampling operation, on the second aligned brain image; a 9-2 step of passing the pre-processed second aligned brain image through the neurovascular anatomy segmentation network; a 9-3 step of performing post-processing of removing an outlier cluster with respect to the second aligned brain image passing through the neurovascular anatomy segmentation network; and a 9-4 step of extracting the cerebrovascular map based on the post-processed second aligned brain image.

In the 9-1 step, the HU windowing operation may be an operation of setting the upper and lower limits of a Hounsfield unit (HU), the HU windowing operation and normalizing operation may be an operation of determining a HU Level from the set lower limit to the upper limit, and mapping the HU level at a determined [0, 1] interval, and the patch sampling operation may be an operation of generating input data by constructing a sub-volume of the 3D volume as a patch for GPU memory utilization, and in the 9-3 step, the outlier cluster removing operation may be an operation of removing the outlier cluster that is not connected but separated on three dimensions.

In the ninth step, the cerebrovascular map may be extracted by dividing an anatomical structure of the artery, and in the tenth step, the information may include data for dividing indications according to a vascular structure.

The indications according to the vascular structure may include large vessel occlusion (LVO) and aneurysm, and in the tenth step, the information may include location information on the cerebrovascular map in which indications are detected and/or predicted, and false-positive related information.

Another aspect of the present disclosure provides a device including a head segmentation unit configured to receive a CT image, predict a bone mask of the skull, a brain mask of the brain, and a brain-related vessel mask by passing the CT image through a head segmentation network capable of separating the skull and the brain, and extract a brain image including only a brain region from the CT image by combining the predicted brain mask and vessel mask; a rigid registration unit configured to receive standardized template data from an atlas unit and receive a brain image from the head segmentation unit by fusing the characteristics of specific samples to be used as a reference for aligning a plurality of data into a common space, perform rigid registration and affine registration between the template data and the brain image to acquire a transformation parameter, and apply rigid warping to the brain image based on the transformation parameter to acquire a first aligned brain image aligned by linear transformation; a non-rigid registration unit configured to extract a deformation field which is a translation vector for each 3D voxel by inputting a 3D volume of the template data and a 3D volume of the first aligned brain image to a pre-learned non-rigid registration network, and acquire a second aligned brain image more accurately registered to the actual brain than a result of the rigid registration unit by performing non-rigid warping that applies grid interpolation in units of voxels to the first aligned brain image based on the deformation field; a neurovascular segmentation unit configured to extract a cerebrovascular map from the second aligned brain image by passing the second aligned brain image through the neurovascular anatomy segmentation network; and a determination unit configured to provide brain-related information based on the cerebrovascular map.

The head segmentation unit may perform pre-processing which is at least one of a resizing operation, a HU windowing operation, and a normalizing operation, with respect to the CT image, pass the pre-processed CT image through the head segmentation network, perform post-processing, which is at least one of a brain VOI crop operation and an outlier cluster removing operation with respect to the CT image passing through the head segmentation network, and predict the bone mask, the brain mask, and the vessel mask based on the post-processed CT image. Here, the resizing operation may be an operation of reducing and/or enlarging an image to a size required by the head segmentation network, the HU windowing operation may be an operation of setting the upper and lower limits of a Hounsfield unit (HU), the normalizing operation may be an operation of determining a HU Level from the set lower limit to the upper limit, and mapping the HU level at a determined [0, 1] interval, the brain VOI crop operation may be an operation of resizing after removing a region other than a volume region of interest for the brain, and the outlier cluster removing operation may be an operation of removing the outlier cluster that is not connected but separated on three dimensions.

The standardized template data of the atlas unit may be generated by aligning the specific sample data in the center so that anatomical patterns or characteristics are preserved and synthesizing the specific sample data after non-rigid registration according to a predetermined level, the rigid warping based on the transformation parameter may apply linear transformations including translation, rotation, and scale transformations so that the brain image is deformed while maintaining an original ratio without distortion, and in the non-rigid warping based on the deformation field, the alignment may be performed to make a shape more consistent with the actual brain by performing detailed secondary alignment on the first aligned brain image based on the transformation parameter by applying the grid interpolation in units of voxels.

First aligned bone mask, brain mask, and vessel mask aligned in a linear transformation may be acquired by applying the rigid warping to the bone mask, the brain mask, and the vessel mask based on the transformation parameter, second aligned bone mask, brain mask, and vessel mask may be acquired by applying non-rigid warping of applying grid interpolation in units of voxels based on the deformation field to the first aligned bone mask, brain mask, and vessel mask, the determination unit may provide the information by further using at least one of the second aligned bone mask, brain mask, and vessel mask based on the cerebrovascular map, the second aligned brain image, and the second aligned bone mask, brain mask, and vessel mask may extract the first aligned brain image and the first aligned bone mask, brain mask, and vessel mask by inversely transforming and applying the deformation field, and the first aligned brain image and the first aligned bone mask, brain mask, and vessel mask may extract the brain image, the bone mask, the brain mask, and the vessel mask by inversely transforming and applying the transformation parameter into a space of the original raw CT image.

The neurovascular segmentation unit may perform pre-processing, which is at least one of a HU windowing operation, a normalizing operation, and a patch sampling operation, on the second aligned brain image, pass the pre-processed second aligned brain image through the neurovascular anatomy segmentation network, perform post-processing of removing an outlier cluster with respect to the second aligned brain image passing through the neurovascular anatomy segmentation network, and extract the cerebrovascular map based on the post-processed second aligned brain image. Here, the HU windowing operation may be an operation of setting the upper and lower limits of a Hounsfield unit (HU), the HU windowing operation and normalizing operation may be an operation of determining a HU Level from the set lower limit to the upper limit, and mapping the HU level at a determined [0, 1] interval, the patch sampling operation may be an operation of generating input data by constructing a sub-volume of the 3D volume as a patch for GPU memory utilization, and the outlier cluster removing operation may be an operation of removing the outlier cluster that is not connected but separated on three dimensions.

All the operations may be performed on GPU/CPU, and if the GPU is used, it is possible to obtain a rate 10 to 100 times faster than CPU.

However, since it is difficult to allocate an entire 3D volume to a GPU memory, input data may be generated by dividing the 3D volume into sub-volumes. Meanwhile, the entire volume may also be used depending on the performance of the installed GPU.

The cerebrovascular map may be extracted by dividing an anatomical structure of the artery, the information may include data for dividing indications according to a vascular structure, the indications according to the vascular structure may include large vessel occlusion (LVO) and aneurysm, and the information provided by the determination unit may include location information on the cerebrovascular map in which indications are detected and/or predicted, and false-positive related information.

According to the present disclosure, it is possible to provide a user with artificial intelligence-based devices and methods for geometric alignment and preprocessing of raw CT images.

According to the present disclosure, it is possible to provide a user with a device and a method capable of minimizing diversity caused by the size and shape, imaging direction, etc. of the patient's skull by applying a process of transforming any raw CT image in a consistent direction and size when the raw CT image has been input.

According to the present disclosure, in a series of processes of taking CT angiography in medical data, since protocols such as an image-taking angle, an image-taking area, a patient orientation, a slice thickness, a slice interval, etc. vary for each situation depending on a vendor of each hospital and habits of the tomographer, it is possible to solve a problem that data have geometrically various variances.

In general, when checking the slices of an axial axis of each data, the anatomical patterns and aspects appearing in each slice are different each time, and in the process of analyzing medical data, data variance appearing according to various imaging protocols is a major cause of lowering accuracy, but the geometrical registration process proposed by the present disclosure may minimize these data variances.

In addition, the method proposed by the present disclosure provides both rigid registration and non-rigid registration results, and an inverse transformation process to the original CTA may also be effective.

According to the present disclosure, when sensitive to a local error according to each characteristic, only linear transformation is applied to use the centrally aligned rigid registration result, and when the region of interest between patients is spatially matched or monitoring is required, a non-rigid registration result may be used.

In addition, the result analyzed on each rigid/non-rigid registration may be inversely transformed into a space of the original CTA to visualize segments or analysis results in the original CTA image.

In addition, in the present disclosure, if specific brain compartments M1 to M6 are used for classification in the original CT image, non-rigid registration is performed, and then standard compartment (M1 to M6) masks of the corresponding space may be applied to be extracted and analyzed. Similarly, inverse transformation to the original CT space may be performed and indicated on the original CT image.

In addition, in the present disclosure, when anatomical information of each vessel and brain region, such as neurovascular anatomy and brain anatomy, is required, a specific region may be distinguished after registration through non-rigid registration. Similarly, inverse transformation to the original CT space may be performed and indicated even on the original CT image.

In addition, in the present disclosure, when monitoring such as aneurysm and tumor is required, the progress of lesions may be shown by matching the images of the same patient taken at different times by performing non-rigid registration.

Meanwhile, effects which can be obtained in the present disclosure are not limited to the aforementioned effects, and other effects, which are not mentioned above, will be apparently understood to a person having ordinary skill in the art from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Hereinafter, a preferred exemplary embodiment of the present disclosure will be described with reference to the drawings. In addition, exemplary embodiments to be described below do not unfairly limit the content of the present disclosure described in claims, and the entire configuration described in the exemplary embodiments cannot be essential as a solution to the present disclosure.

Hereinafter, artificial intelligence-based preprocessing devices and methods according to a preferred exemplary embodiment of the present disclosure will be described in detail with reference to the accompanying drawings.

Problem of Related Art

In order to derive stable performance from a deep learning model, there is a need for minimizing a gap between a learning data distribution and a test data distribution, but to this end, in a learning step, the diversity of train data is augmented and learned, and in a test step, standardized and generalized data are inferred.

A protocol taken for CT images varies greatly depending on a tomographer, a manufacturer, a situation, and a department in charge, but when the protocol is different even for the same patient, a geometric pattern of a taken 3D image is different, so that images shown in 2D axial, coronal, and sagittal cross sections may look different.

Images taken with different protocols each time may be a factor in reducing the diagnostic accuracy from human/deep learning models.

In a series of processes of taking CT angiography in medical data, since protocols such as an imaging angle, an imaging area, a patient orientation, a slice thickness, a slice interval, etc. vary for each situation depending on a vendor of each hospital and habits of the tomographer, data have geometrically various variances.

In general, when the slices of an axial axis of each data are checked, the anatomical patterns and aspects appearing in each slice are different each time.

In the process of analyzing medical data, data variance that appears according to various imaging protocols may be a major cause of lowering accuracy.

Accordingly, the present specification intends to provide a user with artificial intelligence-based devices and methods capable of transforming raw CT images in consistent directions and sizes when the raw CT images have been input, so as to solve the problems.

Specifically, the present disclosure is to provide a user with a device and a method capable of minimizing diversity caused by the size and shape, imaging direction, etc. of the patient's skull by applying a process of transforming any raw CT image in a consistent direction and size when the raw CT image has been input.

Artificial Intelligence Device

Figure 1:
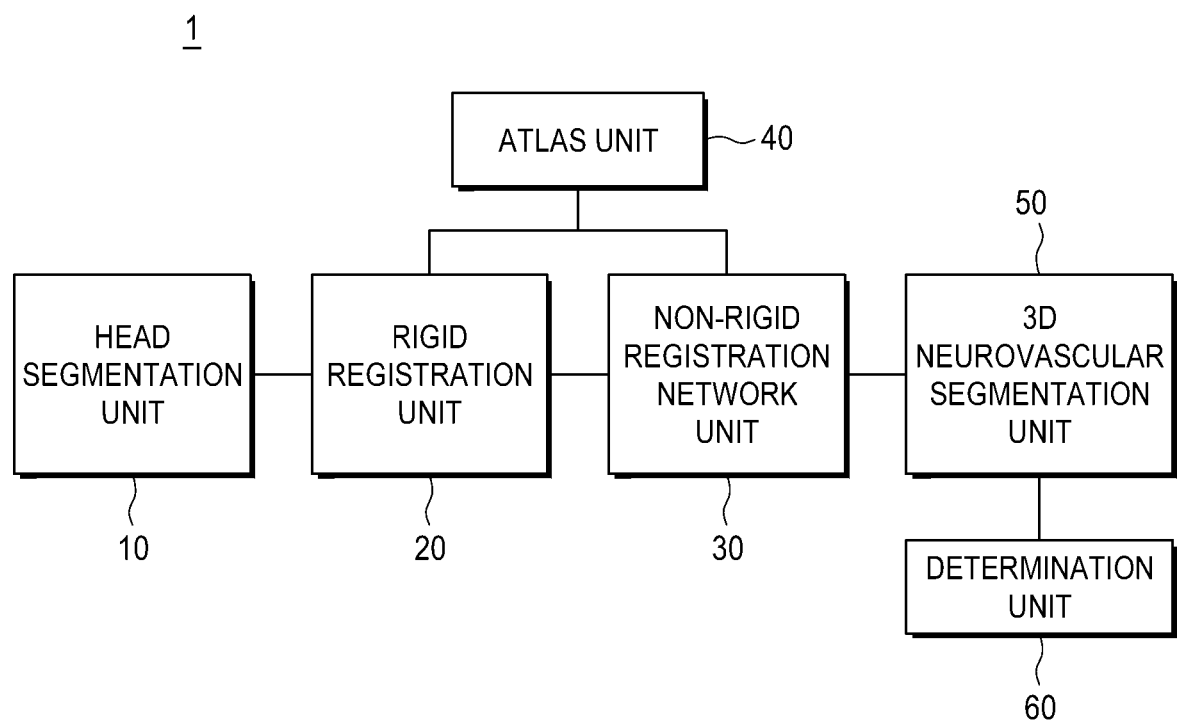
FIG. 1 illustrates examples of a block diagram of a device capable of transforming raw CT images in consistent directions and sizes when the raw CT images have been input, in relation to the present disclosure.

FIG. 1 illustrates examples of a block diagram of a device capable of transforming raw CT images in consistent directions and sizes when the raw CT images have been input, in relation to the present disclosure.

Referring to FIG. 1, an artificial intelligence device 1 provided in the present disclosure may include a head segmentation unit 10, a rigid registration unit 20, a non-rigid registration unit 30, an atlas unit 40, a 3D neurovascular segmentation unit 50, a determination unit 60, and the like.

The head segmentation unit 10 may receive a CT image and pass the CT image through a head segmentation network capable of separating the skull and the brain to predict a bone mask of the skull, a brain mask of the brain, and a brain-related vessel mask.

In addition, the head segmentation unit 10 may extract a brain image including only a brain region from the CT image by combining the predicted brain mask and vessel mask.

Next, the atlas unit 40 generates standardized template data by fusing the characteristics of specific samples to be used as a reference for aligning a plurality of data into a common space and transfers the standardized template data to the rigid registration unit 20.

Here, the standardized template data of the atlas unit is generated by aligning the specific sample data in the center so that anatomical patterns or characteristics are preserved and synthesizing the specific sample data after non-rigid registration according to a predetermined level.

In addition, the rigid registration unit 20 receives the standardized template data from the atlas unit 40, and receives a brain image from the head segmentation unit 10.

Thereafter, the rigid registration unit 20 performs rigid registration and affine registration between the template data and the brain image to acquire a transformation parameter.

In addition, the rigid registration unit 20 applies rigid warping to the brain image based on the transformation parameter to acquire a first aligned brain image aligned by a linear transformation.

The rigid warping based on the transformation parameter applies linear transformations including translation, rotation, and scale transformations so that the brain image is deformed while maintaining an original ratio without distortion.

Meanwhile, the non-rigid registration unit 30 may extract a deformation field which is a translation vector for each 3D voxel by inputting a 3D volume of the template data and a 3D volume of the first aligned brain image to a pre-learned non-rigid registration network.

In addition, the non-rigid registration unit 30 may acquire a second aligned brain image more accurately registered to the actual brain than a result of the rigid registration unit by performing non-rigid warping that applies grid interpolation in units of voxels to the first aligned brain image based on the deformation field.

In the non-rigid warping based on the deformation field, the alignment is performed to make a shape more consistent with the actual brain by performing detailed second alignment on the first aligned brain image based on the transformation parameter by applying the grid interpolation in units of voxels.

Thereafter, the 3D neurovascular segmentation unit 50 may extract a cerebrovascular map from the second aligned brain image by passing the second aligned brain image through a neurovascular anatomy segmentation network.

In addition, the determination unit 60 may provide brain-related information based on the cerebrovascular map.

Here, the cerebrovascular map may be extracted by dividing an anatomical structure of the artery.

In addition, the brain-related information may include data for dividing indications according to a vascular structure.

Representatively, the indications according to the vascular structure include large vessel occlusion (LVO), aneurysm, and the like.

In addition, the information provided by the determination unit 60 may also include location information on the cerebrovascular map in which indications are detected and/or predicted, and false-positive related information.

Hereinafter, the head segmentation unit 10, the rigid registration unit 20, the non-rigid registration unit 30, the atlas unit 40, and the 3D neurovascular segmentation unit 50 will be described in more detail with reference to the drawings.

Head Segmentation Unit

Figure 2:
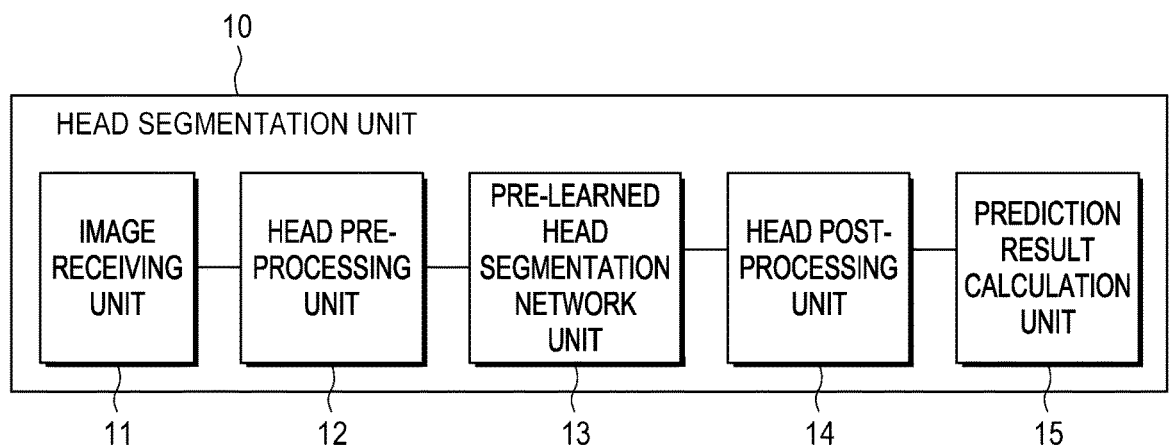
FIG. 2 illustrates an example of a block diagram of a head segmentation unit described in FIG. 1.

FIG. 2 illustrates an example of a block diagram of the head segmentation unit described in FIG. 1.

Referring to FIG. 2, the head segmentation unit 10 may include an image receiving unit 11, a head pre-processing unit 12, a pre-learned head segmentation network unit 13, a head post-processing unit 14, and a prediction result calculation unit 15.

Since a region of interest to be analyzed by the present disclosure is the brain, and the thickness and shape of the skull vary from person to person, the head segmentation unit 10 may perform an operation of predicting each bone, brain, and vessel mask by passing through a deep learning-based head segmentation network capable of separating the skull and brain regions and then extracting a whole brain region from the original CT image by combining the brain mask and the vessel mask.

First, the image receiving unit 11 receives a CT image from external equipment.

Next, the head pre-processing unit 12 divides a 3D image of a raw CT image into 2D axial slices, and then concatenates adjacent slices of a slice to be segmented to constitute input data.

Specifically, the input data is input to the pre-learned head segmentation network unit 13 through pre-processing of the head pre-processing unit 12.

The head pre-processing unit 12 may perform operations such as (1) resizing, (2) HU windowing, (3) normalizing, and the like.

The (1) resizing operation is an operation of reducing and/or enlarging an image to a size required by the head segmentation network.

Next, the (2) HU windowing operation is an operation of setting the upper and lower limits of a Hounsfield unit (HU).

In addition, the normalizing operation is an operation of determining a HU Level from the set lower limit to an upper limit, and mapping the HU Level to a determined [0, 1] interval. Representatively, a method of mapping the HU Level from the lower limit to the upper limit of HU windowing at an interval of [0, 1] may be applied.

The pre-processed CT image passes through the pre-learned head segmentation network unit 13, and with respect to the CT image passing through the head segmentation network unit 13, the head post-processing unit 14 performs post-processing, which is at least one of a brain VOI crop operation and an outlier cluster removing operation.

The pre-learned head segmentation network unit 13 is a deep learning-based segmentation network pre-learned for skull and brain regions so as to extract a brain region, which is a region of interest.

Here, the brain VOI crop operation is an operation of resizing after removing a region other than a volume region of interest for the brain.

In addition, the outlier cluster removing operation is an operation of removing a small outlier cluster that is not connected but separated on three dimensions.

Thereafter, the prediction result calculation unit 15 predicts the bone mask, the brain mask, and the vessel mask based on the post-processed CT image.

That is, the prediction result calculation unit 15 may predict the bone mask of the skull, the brain mask of the brain, and the brain-related vessel mask, and extract a brain image including only a brain region from a first input CT image by combining the predicted brain mask and vessel mask.

Rigid Registration Unit, Non-Rigid Registration Unit and Atlas Unit

Figure 3:
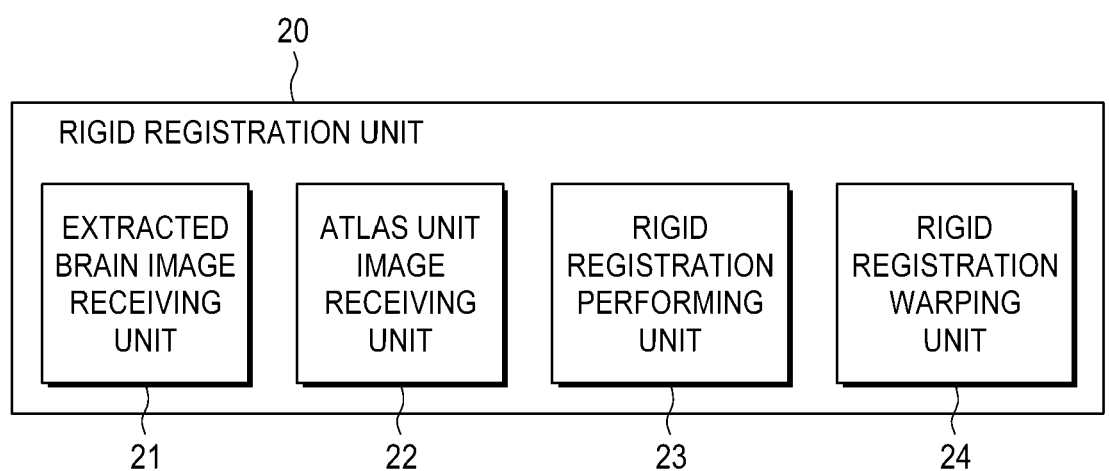
FIG. 3 illustrates an example of a block diagram of a rigid registration unit described in FIG. 1.

FIG. 3 illustrates an example of a block diagram of the rigid registration unit described in FIG. 1.

Referring to FIG. 3, the rigid registration unit 20 includes an extracted brain image receiving unit 21, an atlas unit image receiving unit 22, a rigid registration performing unit 23, a rigid registration warping unit 24.

Preemptively, the standardized template data of the atlas unit 40 is generated by aligning the specific sample data in the center so that anatomical patterns or characteristics are preserved and synthesizing the specific sample data after non-rigid registration according to a predetermined level.

The atlas unit image receiving unit 22 receives standardized template data from the atlas unit 40, and the extracted brain image receiving unit 21 receives a brain image including only an extracted brain region from the head segmentation unit 10.

The rigid registration performing unit 23 may acquire a transformation parameter by performing rigid registration and affine registration between the template data and the brain image.

Thereafter, the rigid registration warping unit 24 may acquire a first aligned brain image aligned by linear transformation by applying rigid warping to the brain image based on the transformation parameter.

In summary, in the rigid registration warping unit 24, the rigid warping based on the transformation parameter may apply linear transformations including translation, rotation, and scale transformations so that the brain image is deformed while maintaining an original ratio without distortion.

Figure 4:
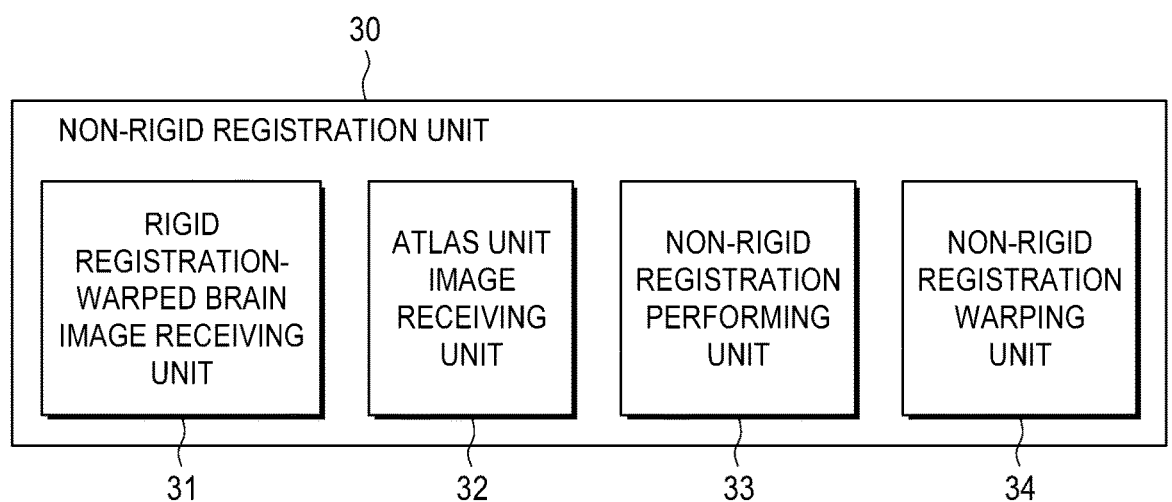
FIG. 4 illustrates an example of a block diagram of a non-rigid registration unit described in FIG. 1.

Meanwhile, FIG. 4 illustrates an example of a block diagram of the non-rigid registration unit described in FIG. 1.

Referring to FIG. 4, the non-rigid registration unit 30 includes a rigid registration-warped brain image receiving unit 31, an atlas unit image receiving unit 32, a non-rigid registration performing unit 33 and a non-rigid registration warping unit 34.

First, the atlas unit image receiving unit 32 receives standardized template data from the atlas unit 40, and the rigid registration-warped brain image receiving unit 31 acquires the first aligned brain image which is a result of the rigid registration warping unit 24.

Thereafter, the non-rigid registration performing unit 33 may extract a deformation field which is a translation vector for each 3D voxel by inputting a 3D volume of the template data and a 3D volume of the first aligned brain image to a pre-learned non-rigid registration network.

In addition, the non-rigid registration warping unit 34 may acquire a second aligned brain image more accurately registered to the actual brain than a result of the rigid registration unit by performing non-rigid warping that applies grid interpolation in units of voxels to the first aligned brain image based on the deformation field.

In summary, in the non-rigid warping based on the deformation field, the alignment is performed to make a shape more consistent with the actual brain by performing detailed second alignment on the first aligned brain image based on the transformation parameter by applying the grid interpolation in units of voxels.

Therefore, in the present disclosure, when sensitive to a local error according to each characteristic, only linear transformation is applied to use the centrally aligned rigid registration result, and at the same time, when the region of interest between patients is spatially matched or monitoring is required, a non-rigid registration result is used.

The reason why the present disclosure uses rigid registration and non-rigid registration together will be described in detail.

Figure 5A:
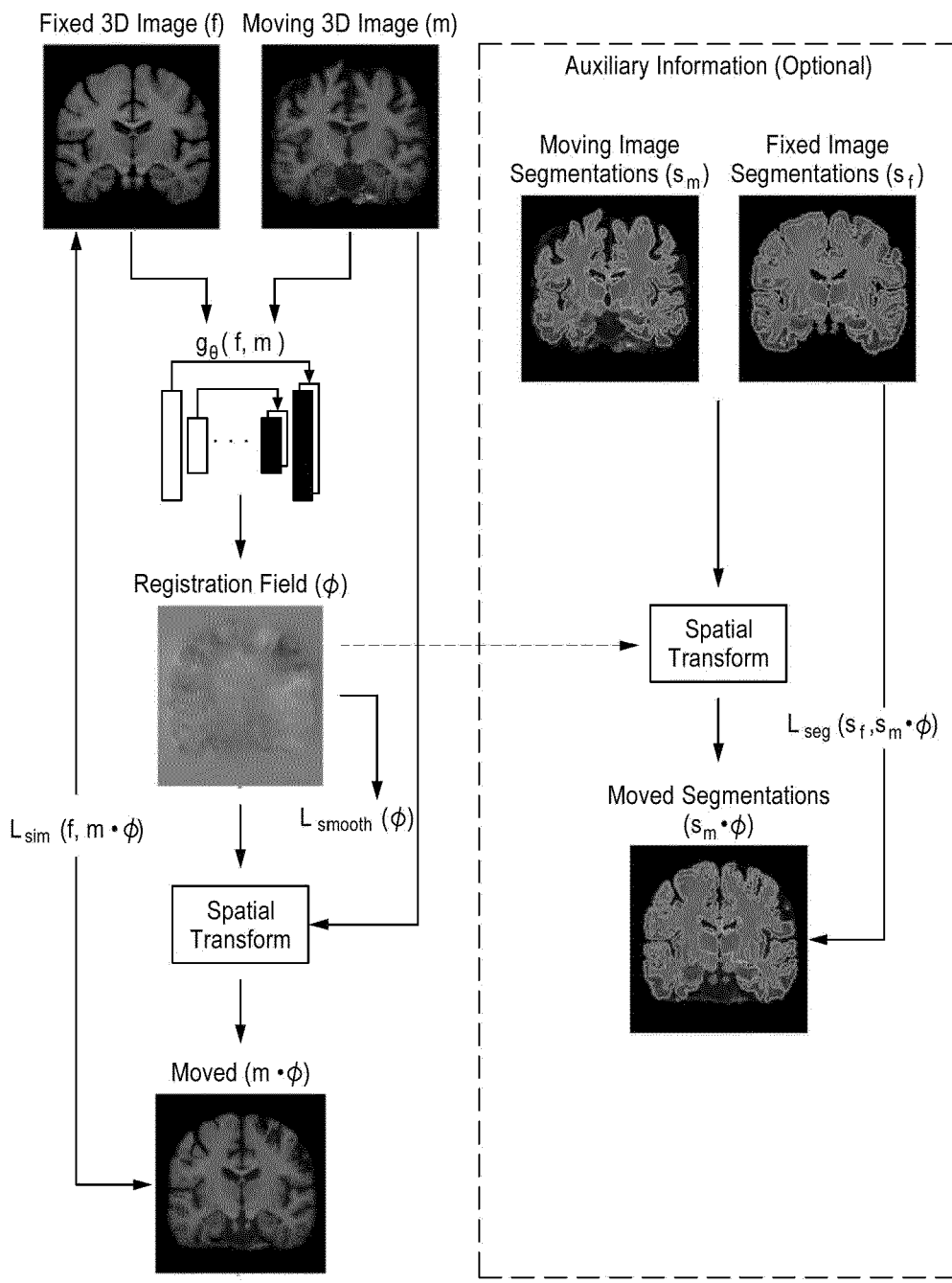
FIGS. 5A and 5B are diagrams for describing applications of rigid registration and non-rigid registration.
Figure 5B:
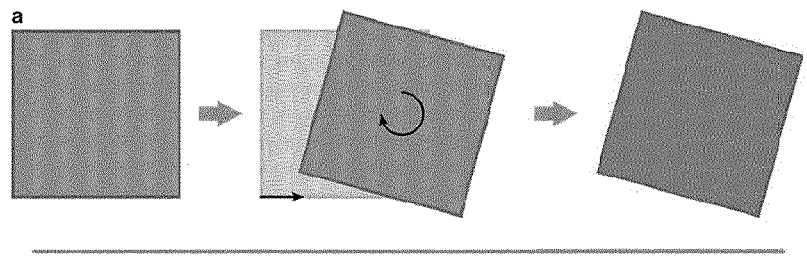
Figure 5B:
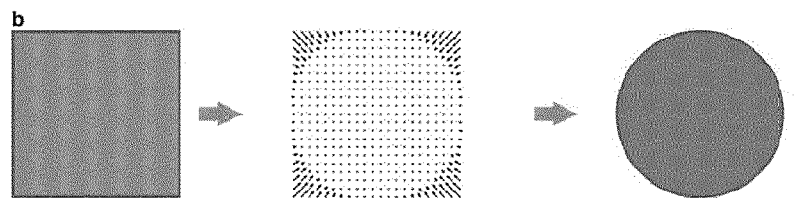

FIGS. 5A and 5B are diagrams for describing applications of rigid registration and non-rigid registration.

Referring to FIG. 5A, an object of rigid registration aims to acquire an affine matrix from 2D/3D data.

Only linear transformations such as translation, rotation, and scale transformations are enabled, and a translation target is deformed while maintaining an original ratio (without distortion).

In addition, an object of non-rigid registration aims to acquire a translation vector field (deformation field) in pixel units from 2D/3D data.

Since it is determined where warping is to be performed in pixel units, all types of transformation are possible, thereby increasing detailed matching compared to rigid registration.

FIG. 5B (a) illustrates an example of rigid registration transformation, and FIG. 5A (b) illustrates an example of non-rigid registration transformation.

However, since non-rigid registration itself is specialized for local deformation, there is a problem in that deformation with a large translation radius is difficult.

Accordingly, in the present disclosure, a method of using non-rigid registration is applied when performing detailed second alignment after aligning the distorted center with rigid registration.

Representatively, a method of performing non-rigid registration may be performed through well-known deep learning-based VoxelMorph.

The corresponding method may show at least 100 times faster speed and higher accuracy than an existing classic non-rigid registration method.

Figure 6A:
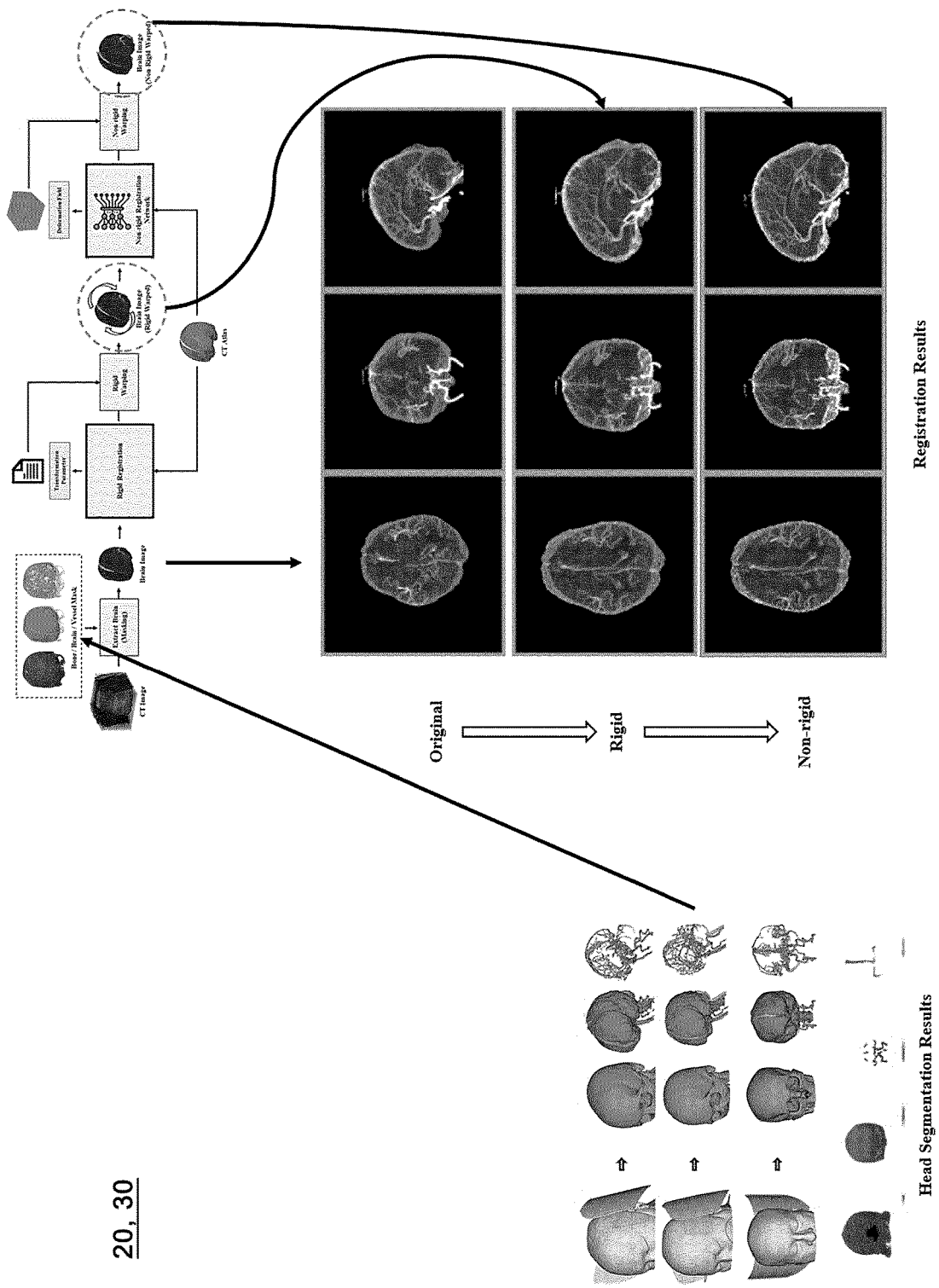
FIGS. 6A and 6B are diagrams illustrating results of more stably matching edges, vessels, anatomical structures, etc. by applying rigid registration and non-rigid registration together.
Figure 6B:
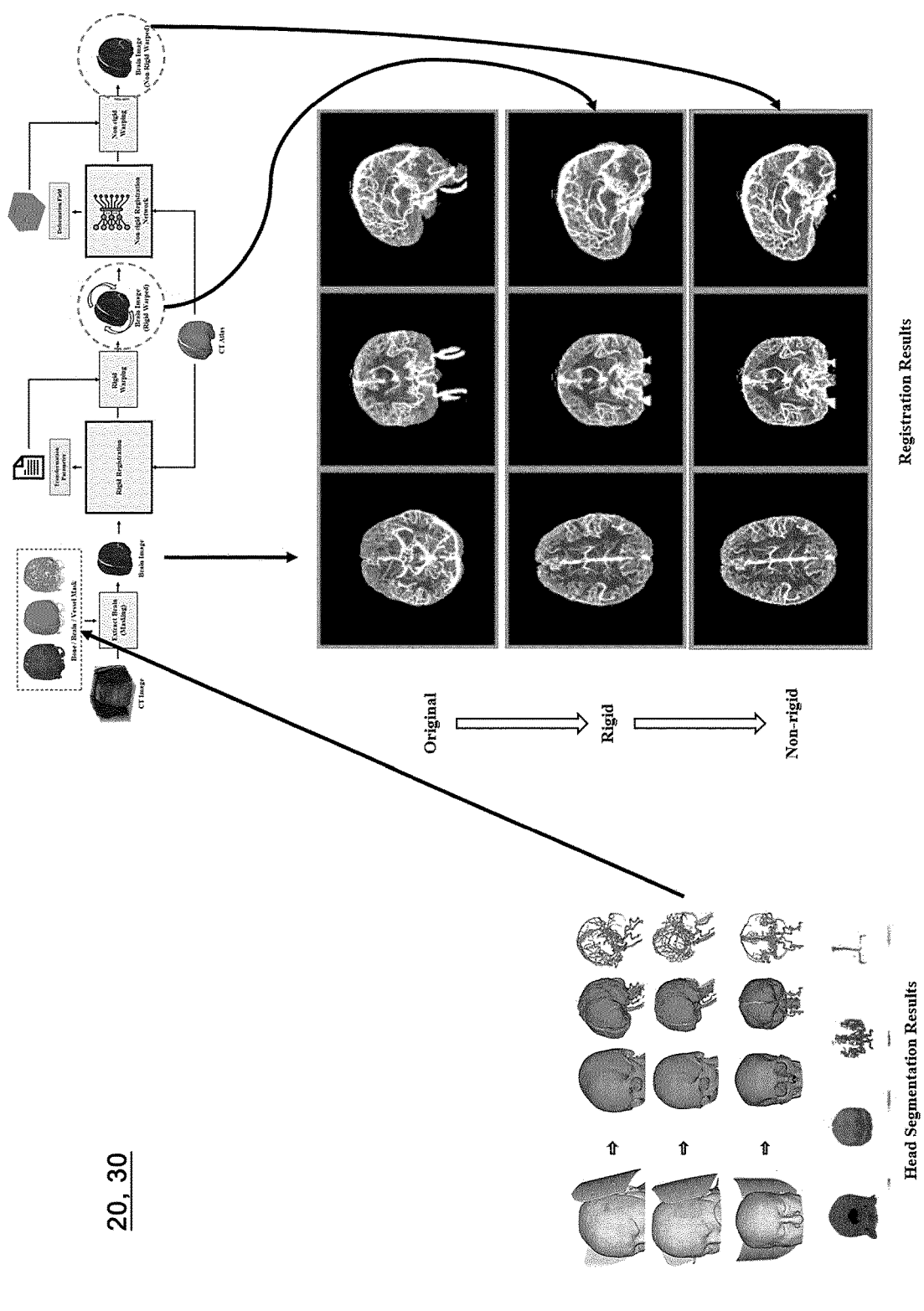

FIGS. 6A and 6B are diagrams illustrating results of more stably matching edges, vessels, anatomical structures, etc. by applying rigid registration and non-rigid registration together.

Referring to FIGS. 6A and 6B, in the case of original CTA, tendency for two wobbles to be large and out of alignment may be seen.

In addition, as a result of rigid registration, the center is aligned and a stable result is shown compared to original CTA, but if there is a difference in brain shape, it may be confirmed that slight deformation is seen.

If a result of applying non-rigid registration to the rigid registration result, a result that mostly coincides with the contents of the actual brain may be shown.

That is, when the two methods are sequentially applied, edges, vessels, anatomical structures, etc. may be matched more stably than when only rigid registration has been performed.

In addition, atlas used when applying rigid registration and non-rigid registration methods will be described.

Figure 7:
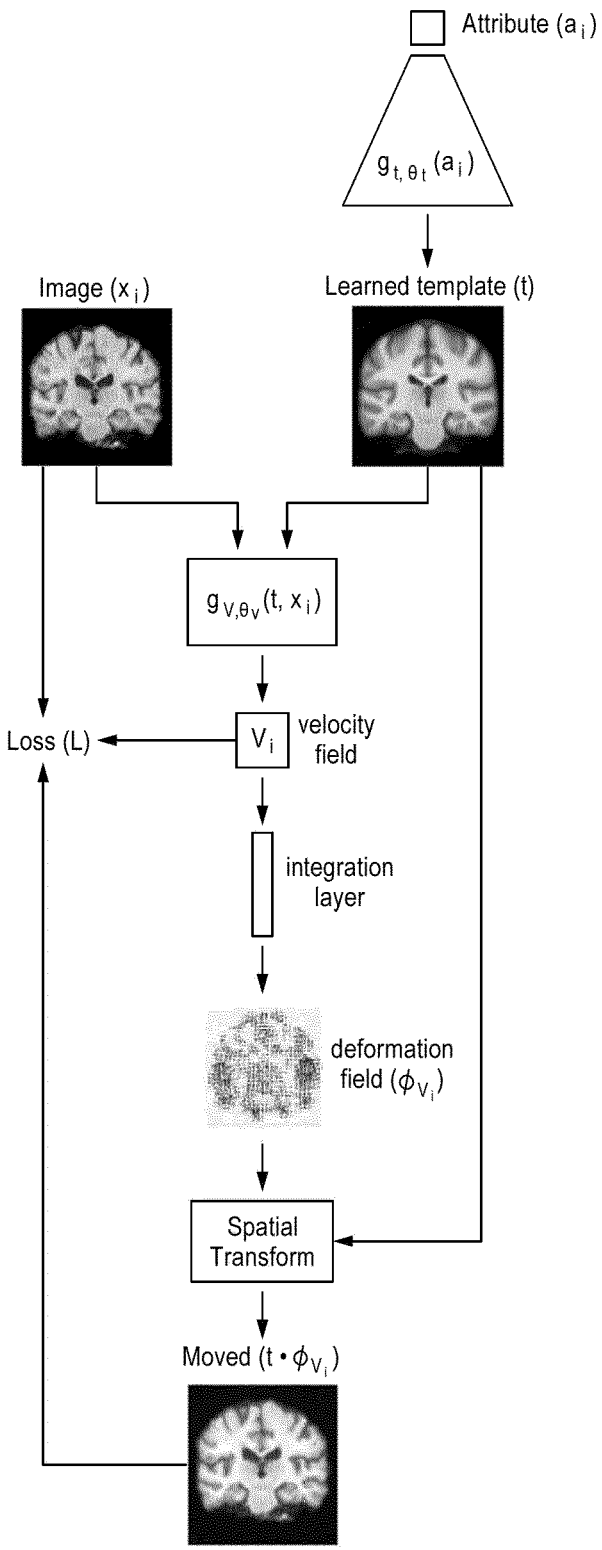
FIG. 7 is a diagram illustrating a process of generating standardized template data of an atlas unit applied to the present disclosure.

FIG. 7 is a diagram illustrating a process of generating standardized template data of the atlas unit applied to the present disclosure.

In a medical field, atlas (template) is data standardized by fusing the characteristics of specific samples, and is generally used as a reference for aligning various data into a common space through registration.

In the case of MRI data, there is a standardized atlas called MNI, but in the case of CT, such a standardized atlas does not exist, and thus a process of newly generating the atlas is required.

Referring to FIG. 7, as an atlas generation method, to 50 CTAs with normal or specific indications may be set as samples and applied.

Here, since anatomical patterns or characteristics need to be preserved, the atlas may be configured to be matched at a certain level by aligning each initial sample data to the center.

Thereafter, classic non-rigid registration is performed to be very closely matched, and then the atlas may be generated by fusing each data well.

In the present disclosure, since the classic non-rigid registration has a disadvantage of taking a long time and being difficult to succeed, a deep learning-based generative model is used. The corresponding deep learning model is learned to generate an optimized non-rigid template/atlas that may explain each unaligned CTA through unsupervised learning.

Figure 8:
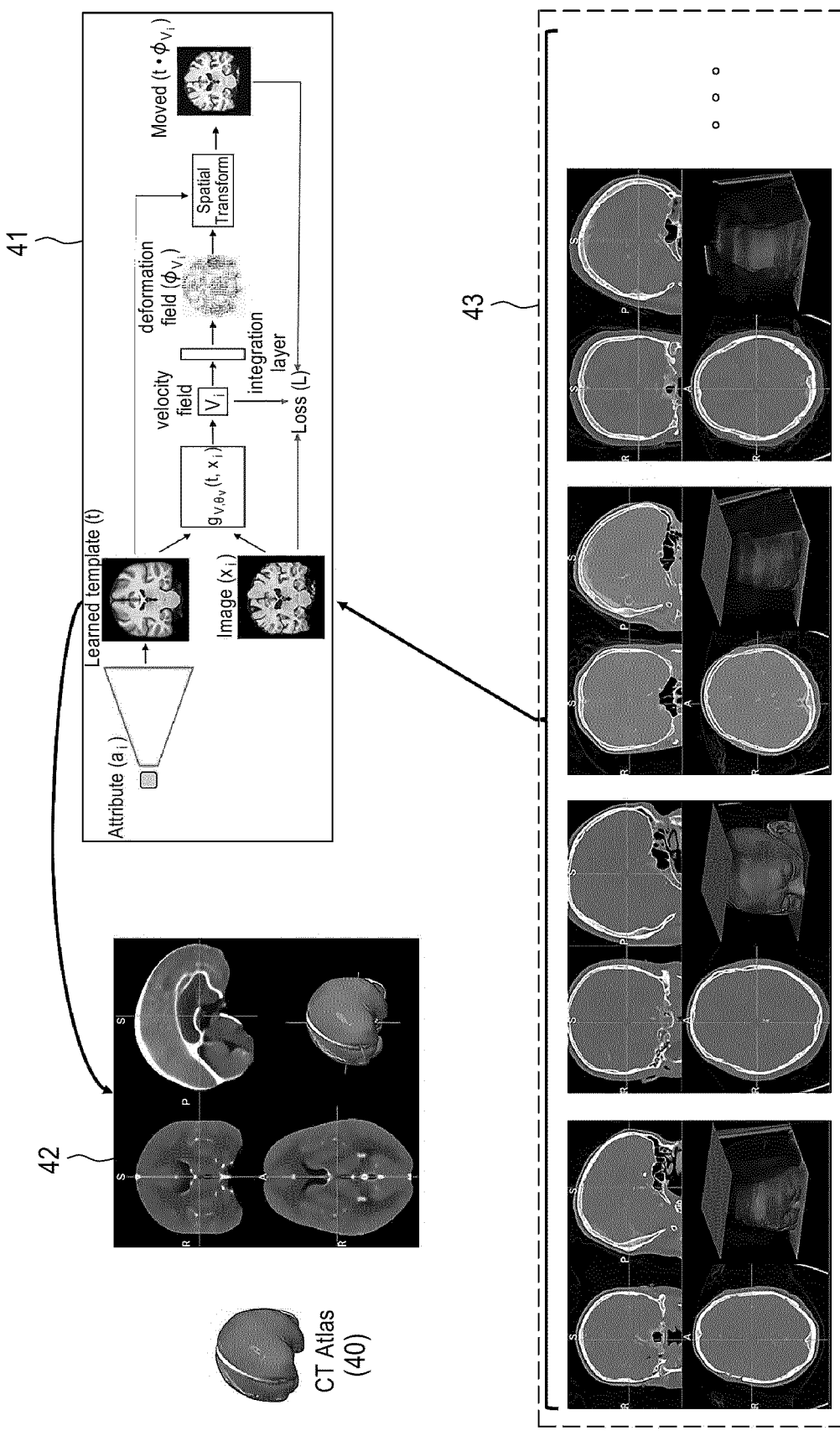
FIG. 8 is a diagram illustrating a result of generating an atlas according to FIG. 7.

FIG. 8 is a diagram illustrating a result of generating the atlas according to FIG. 7.

The atlas generated in FIG. 8 may be post-processed to be left/right symmetric to be applied to rigid registration and non-rigid registration methods.

The proposed atlas, rigid registration and non-rigid registration processes have an advantage of minimizing the aforementioned data variance.

The method proposed by the present disclosure provides both rigid registration and non-rigid registration results, and an inverse transformation process to the original CTA may also be effective.

When sensitive to a local error according to each characteristic, only linear transformation is applied to use the centrally aligned Rigid Registration result, and when the region of interest between patients is spatially matched or monitoring is required, a non-rigid registration result may be used.

In addition, the result analyzed on each rigid/non-rigid registration may be inversely transformed into a space of the original CTA to visualize segments or analysis results in the original CTA image.

In the case of the CT atlas applied to the present disclosure, a non-rigid template/atlas may be extracted by learning a deep learning-based generative model from CTAs of 100 normal groups aligned with rigid/affine, and then applied by using a symmetric template/atlas with left/right symmetry.

In this specification, the template and the atlas may be used interchangeably, and the two terms refer to the same meaning.

In addition, the extracted brain image is obtained as a first aligned image through linear transformation (rotation/scale/translation, etc.) through CT atlas and rigid/affine registration, and thereafter, for more accurate registration, registration in pixel/voxel units is performed through a non-rigid registration model, and the transformation parameter and the deformation field extracted from each registration result may be used to transform each mask and a CT image.

3D Neurovascular Segmentation Unit

The 3D neurovascular segmentation unit 50 extracts a cerebrovascular map through a deep learning-based neurovascular anatomy segmentation network to extract a vascular structure from the aligned brain image.

At this time, unlike the vessel mask, neurovascular anatomy may divide the anatomical structure of each artery, and the determination unit 60 may use neurovascular anatomy to divide indications according to a vascular structure.

Figure 9:
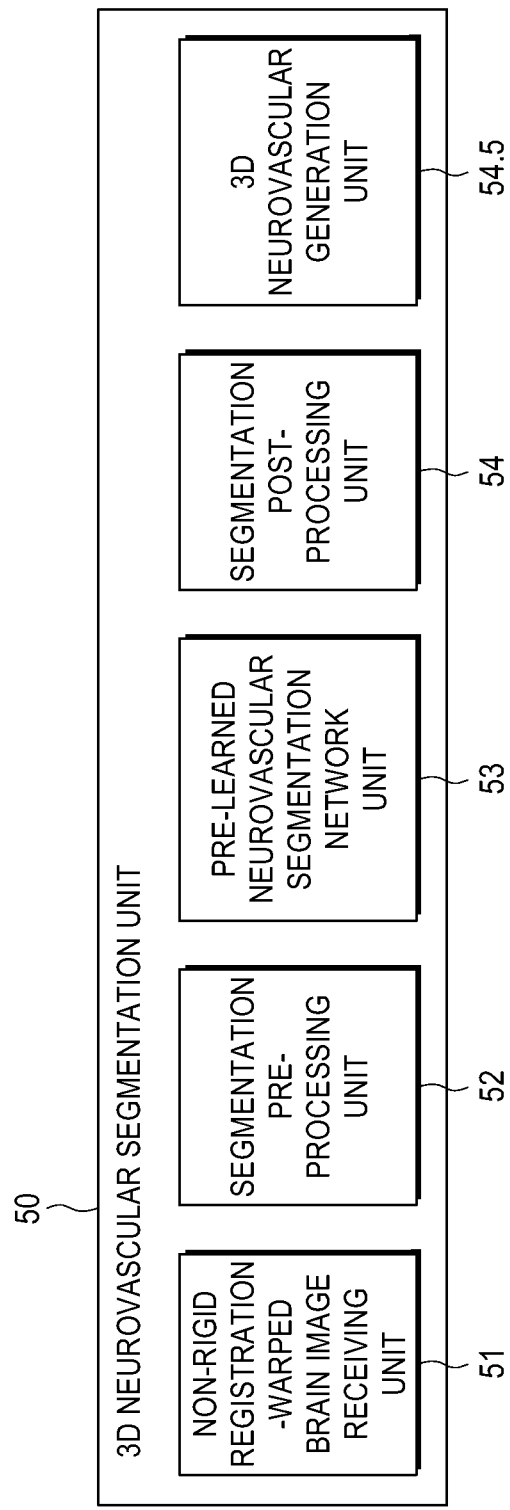
FIG. 9 illustrates an example of a block diagram of a neurovascular segmentation unit described in FIG. 1.

FIG. 9 illustrates an example of a block diagram of the 3D neurovascular segmentation unit described in FIG. 1.

Referring to FIG. 9, the 3D neurovascular segmentation unit 50 may include a non-rigid registration-warped brain image receiving unit 51, a segmentation pre-processing unit 52, a pre-learned neurovascular segmentation network unit 53, a segmentation post-processing unit 54, and a 3D neurovascular generation unit 54.5.

The non-rigid registration-warped brain image receiving unit 51 receives a second aligned brain image from the non-rigid registration unit 30.

Then, the second aligned brain image may pass through a neurovascular anatomy segmentation network, and the pre-processed input data may generate neurovascular anatomy through the segmentation network prediction and post-processing.

The segmentation pre-processing unit 52 may perform pre-processing, which is at least one of a HU windowing operation, a normalizing operation, and a patch sampling operation, on the second aligned brain image.

The HU windowing operation is an operation of setting the upper and lower limits of a Hounsfield unit (HU).

In addition, the normalizing operation is an operation of determining a HU Level from the set lower limit to an upper limit, and mapping the HU Level to a determined [0, 1] interval.

In addition, the patch sampling operation is an operation of generating input data by constructing a sub-volume of the 3D volume as a patch for GPU memory utilization.

All the operations may be performed on GPU/CPU, and if the GPU is used, it is possible to acquire a rate 10 to 100 times faster than CPU. However, since it is difficult to allocate an entire 3D volume to a GPU memory, input data is generated by dividing the 3D volume into sub-volumes. Meanwhile, the entire volume may also be used depending on the performance of the installed GPU.

Here, the pre-processed second aligned brain image passes through the neurovascular anatomy segmentation network 53, and the segmentation post-processing unit 54 performs the post-processing of removing an outlier cluster with respect to the second aligned brain image passing through the neurovascular anatomy segmentation network 53.

The outlier cluster removing operation is an operation of removing the outlier cluster that is not connected but separated on the three dimensions.

In addition, the 3D neurovascular generation unit 54.5 extracts the cerebrovascular map based on the post-processed second aligned brain image.

The neurovascular anatomy extracted from the model may be used to visualize a position in the results of detecting and predicting indications for each vessel, such as large vessel occlusion (LVO) and aneurysm, or to suppress false-positive prediction.

That is, the information provided by the determination unit 60 may further include location information on the cerebrovascular map in which indications are detected and/or predicted, and false-positive related information.

Artificial Intelligence Method

Figure 10:
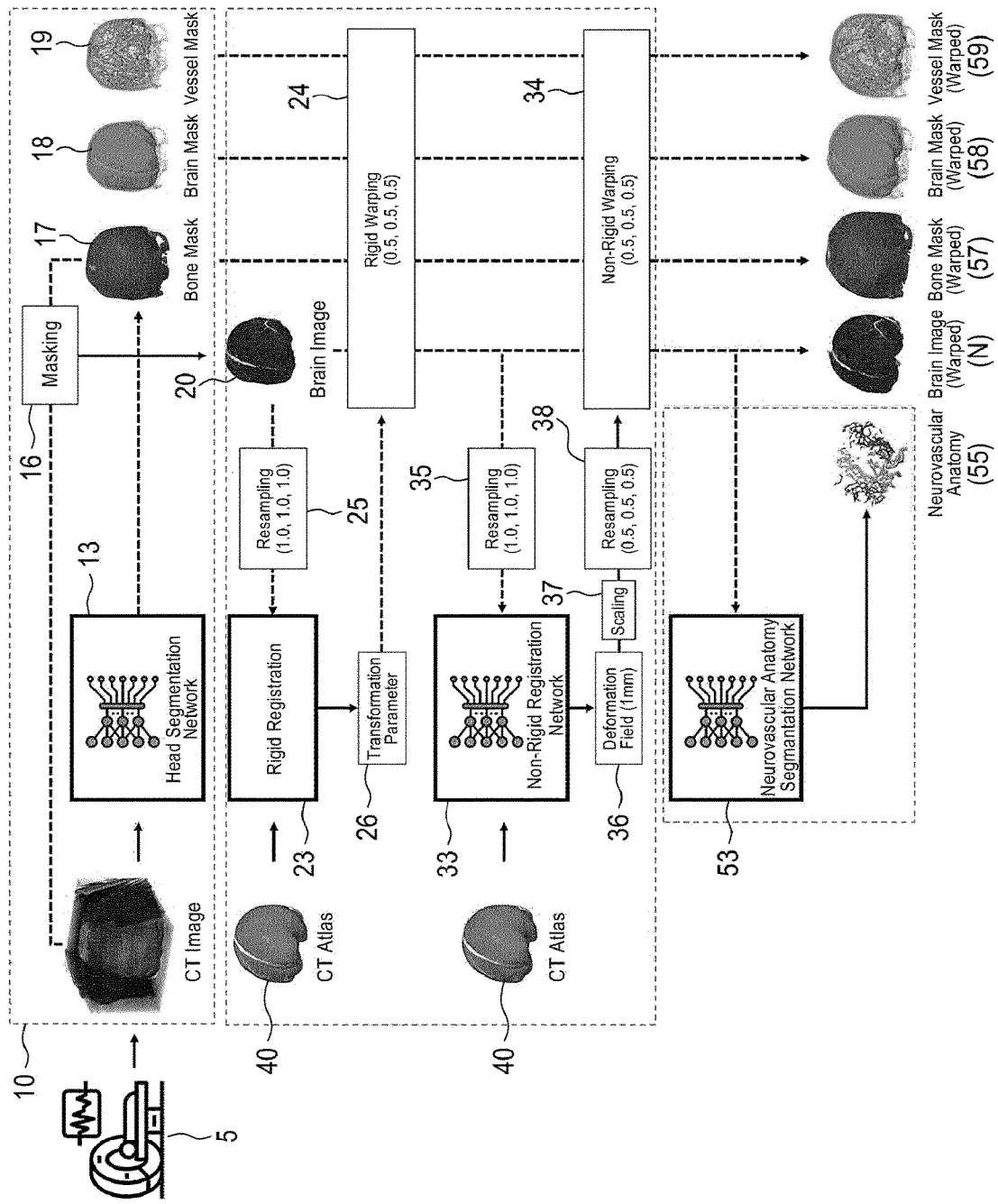
FIG. 10 illustrates a flowchart of a method capable of transforming raw CT images in consistent directions and sizes when the raw CT images have been input, in relation to the present disclosure.

FIG. 10 illustrates a flowchart of a method capable of transforming raw CT images in consistent directions and sizes when the raw CT images have been input, in relation to the present disclosure.

As described above, the method proposed by the present disclosure is divided into (1) a raw CT image segmentation operation, (2) a registration operation, and (3) a neurovascular anatomy segmentation operation.

(1) Raw CT Image Segmentation Operation

Our region of interest is the brain, and the thickness and shape of the skull vary from person to person. Accordingly, each bone, brain, and vessel mask is predicted by passing through the head segmentation network capable of separating the skull and brain regions, and then the brain mask and the vessel mask are combined to extract the whole brain region from the original CT image.

(2) Registration Operation

The extracted brain image obtains a first aligned image through linear transformation (rotation/scale/translation, etc.) through CT atlas and rigid/affine registration. Then, for more accurate registration, registration is performed in pixel/voxel units through the non-rigid registration model. The transformation parameter and the deformation field extracted from each registration result are used to transform each mask and CT image.

(3) Neurovascular Anatomy Segmentation Operation

A cerebrovascular map is extracted through the neurovascular anatomy segmentation network so as to extract a vascular structure from the aligned brain image. Unlike the vessel mask, neurovascular anatomy divides the anatomy structure of each artery. The neurovascular anatomy may be used later to divide indications according to a vascular structure.

Referring to FIG. 10, a method according to the present disclosure will be described in more detail.

Referring to FIG. 10, the head segmentation unit 10 receives a CT image, and the pre-learned head segmentation network unit 13 separates the skull and brain from the CT image, and predicts a bone mask 17 of the skull, a brain mask 18 of the brain, and a brain-related vessel mask 19.

In addition, the head segmentation unit 10 may extract a brain image K including only a brain region from the CT image by combining 16 the predicted brain mask and vessel mask.

Thereafter, the rigid registration unit 20 fuses the characteristics of specific samples to be used as a reference for aligning a plurality of data into a common space to receive standardized template data from the atlas unit 40 and receive the brain image K from the head segmentation unit 10.

The rigid registration performing unit 23 and the rigid registration warping unit 24 of the rigid registration unit 20 perform rigid registration and affine registration between the template data and the brain image K to acquire a transformation parameter 26.

In addition, the rigid registration unit 20 applies rigid warping 24 to the brain image K based on the transformation parameter 26 to acquire a first aligned brain image R aligned by linear transformation.

In addition, the non-rigid registration unit 30 receives the fused standardized template data from the atlas unit 40, and receives the first aligned brain image R from the rigid registration unit 20.

Thereafter, the non-rigid registration performing unit 33 may extract a deformation field 36 which is a translation vector for each 3D voxel by inputting a 3D volume of the template data and a 3D volume of the first aligned brain image to a pre-learned non-rigid registration network.

In addition, the non-rigid registration warping unit 34 may acquire a second aligned brain image N more accurately registered to the actual brain by performing non-rigid warping 34 that applies 37 and 38 grid interpolation in units of voxels to the first aligned brain image R based on the deformation field.

Thereafter, the neurovascular segmentation unit 50 may extract a cerebrovascular map 55 from the second aligned brain image by passing the second aligned brain image N through the neurovascular anatomy segmentation network 53.

Thereafter, the determination unit 60 may provide brain-related information based on the cerebrovascular map.

Meanwhile, the rigid registration unit 20 can acquire first aligned bone mask, brain mask, and vessel mask aligned in linear transformation by applying the rigid warping 24 based on the transformation parameter 26 to the bone mask 17, the brain mask 18, and the vessel mask 19.

In addition, the non-rigid registration unit 30 may acquire second aligned bone mask 57, brain mask 58, and vessel mask 59 by applying the non-rigid warping 34 of applying grid interpolation in units of voxels based on the deformation field 36 to the first aligned bone mask, brain mask, and vessel mask.

The determination unit 60 may also provide information by further using at least one of the second aligned bone mask 57, brain mask 58, and vessel mask 59 based on the cerebrovascular map 55.

On the contrary, the second aligned brain image N, and the second aligned bone mask 57, brain mask 58, and vessel mask 59 can extract the first aligned brain image R and the first aligned bone mask, brain mask, and vessel mask by inversely transforming and applying the deformation field 36.

Furthermore, the first aligned brain image R and the first aligned bone mask, brain mask, and vessel mask may also extract the brain image K, the bone mask 17, the brain mask 18, and the vessel mask 19 in a space of the original raw CT image by inversely transforming and applying the transformation parameter 26.

Operation of Head Segmentation Unit

Figure 11:
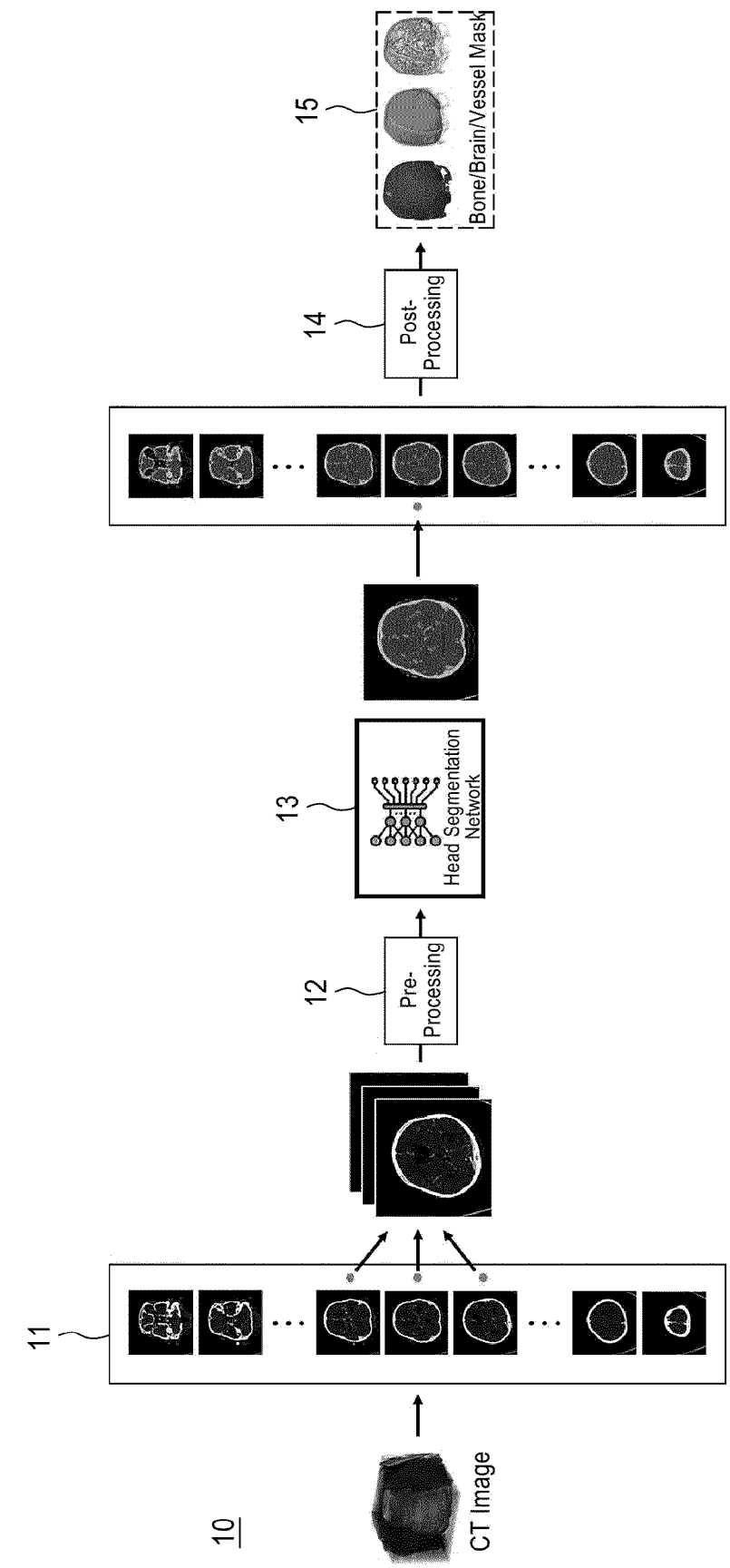
FIG. 11 illustrates an operation of a head segmentation unit described in FIG. 10 over time.

FIG. 11 illustrates an operation of the head segmentation unit described in FIG. 10 over time.

Referring to FIG. 10, the image receiving unit 11 receives a CT image from external equipment.

Next, the head pre-processing unit 12 divides a 3D image of a raw CT image into 2D axial slices, and then concatenates adjacent slices of a slice to be segmented to constitute input data.

Specifically, the input data is input to the pre-learned head segmentation network unit 13 through pre-processing of the head pre-processing unit 12.

The head pre-processing unit 12 may perform operations such as (1) resizing, (2) HU windowing, (3) normalizing, and the like.

The pre-processed CT image passes through the pre-learned head segmentation network unit 13, and with respect to the CT image passing through the head segmentation network unit 13, the head post-processing unit 14 performs post-processing, which is at least one of a brain VOI crop operation and an outlier cluster removing operation.

Thereafter, the prediction result calculation unit predicts information 15 including the bone mask 17, the brain mask 18, and the vessel mask 19 based on the post-processed CT image.

That is, the prediction result calculation unit 15 may predict the bone mask 17 of the skull, the brain mask 18 of the brain, and the brain-related vessel mask 19, and extract a brain image K including only a brain region from a first input CT image by combining the predicted brain mask 18 and vessel mask 19.

Operation of Rigid Registration Unit and Non-Rigid Registration Unit

Figure 12:
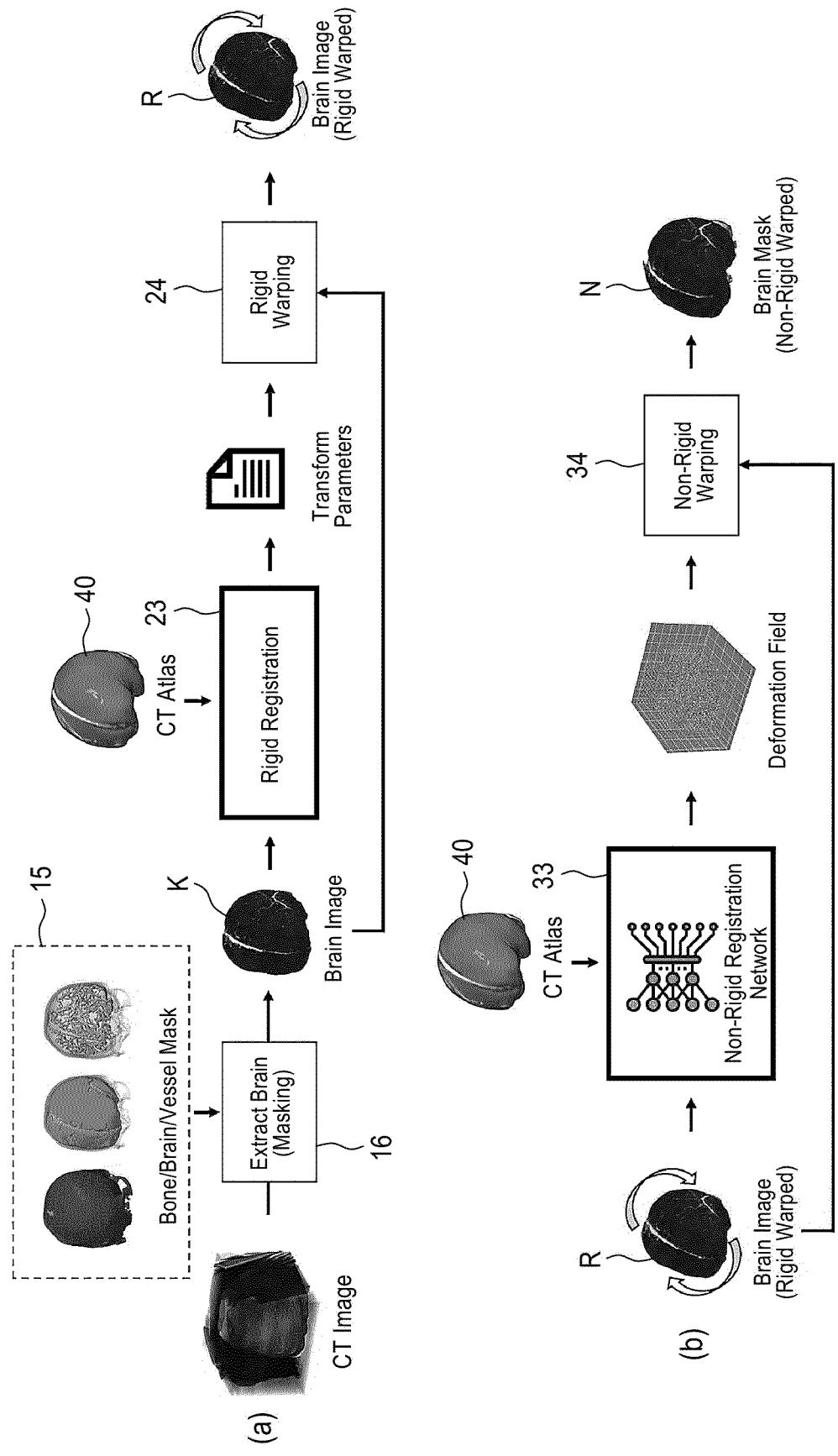
FIG. 12 illustrates operations of a rigid registration unit and a non-rigid registration unit described in FIG. 10 over time.

FIG. 12 illustrates operations of the rigid registration unit and the non-rigid registration unit described in FIG. 10 over time.

Referring to FIG. 12A, the atlas unit image receiving unit 22 receives standardized template data from the atlas unit 40, and the extracted brain image receiving unit 21 receives a brain image K including only an extracted brain region from the head segmentation unit 10.

The rigid registration performing unit 23 may acquire a transformation parameter by performing rigid registration and affine registration between the template data and the brain image.

Thereafter, the rigid registration warping unit 24 may acquire a first aligned brain image R aligned by linear transformation by applying rigid warping to the brain image based on the transformation parameter.

In summary, in the rigid registration warping unit 24, the rigid warping based on the transformation parameter may apply linear transformations including translation, rotation, and scale transformations so that the brain image is deformed while maintaining an original ratio without distortion.

In addition, referring to FIG. 12B, the atlas unit image receiving unit 32 receives standardized template data from the atlas unit 40, and the rigid registration-warped brain image receiving unit 31 acquires the first aligned brain image R which is a result of the rigid registration warping unit 24.

Thereafter, the non-rigid registration performing unit 33 may extract a deformation field which is a translation vector for each 3D voxel by inputting a 3D volume of the template data and a 3D volume of the first aligned brain image to a pre-learned non-rigid registration network.

In addition, the non-rigid registration warping unit 34 may acquire a second aligned brain image N more accurately registered to the actual brain than a result of the rigid registration unit by performing non-rigid warping that applies grid interpolation in units of voxels to the first aligned brain image based on the deformation field.

In summary, in the non-rigid warping based on the deformation field, the alignment is performed to make a shape N more consistent with the actual brain by performing detailed second alignment on the first aligned brain image R based on the transformation parameter by applying the grid interpolation in units of voxels.

Figure 13:
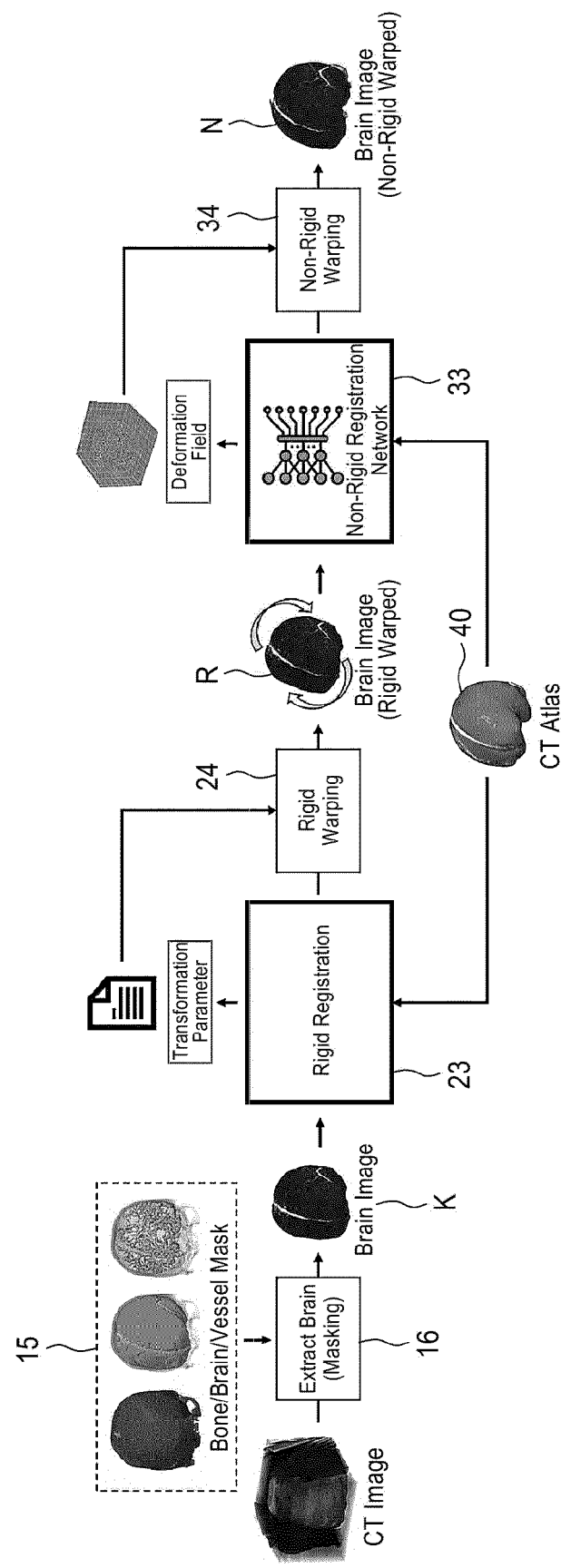
FIG. 13 illustrates a process of combining and processing the operations of the rigid registration unit and the non-rigid registration unit described in FIG. 12 over time.

FIG. 13 illustrates a process of combining and processing the operations of the rigid registration unit and the non-rigid registration unit described in FIG. 12 over time.

As illustrated in FIG. 13, in the present disclosure, when sensitive to a local error according to each characteristic, only linear transformation is applied to use the centrally aligned rigid registration result, and at the same time, when the region of interest between patients is spatially matched or monitoring is required, a non-rigid registration result is used.

The reason why the present disclosure uses rigid registration and non-rigid registration together is as described above. That is, only linear transformation such as translation, rotation, and scale transformations is possible, and the present disclosure is to simultaneously apply a rigid registration effect, in which the translation target is deformed while maintaining its original ratio (without distortion), and a non-rigid registration effect, which obtains a translation vector field (deformation field) in pixel units from 2D/3D data.

In the case of non-rigid registration, since it is determined where warping is to be performed in pixel units, all types of transformation are possible, thereby increasing detailed matching compared to rigid registration.

FIG. 5B (a) illustrates an example of rigid registration transformation, and FIG. 5B (b) illustrates an example of non-rigid registration transformation.

However, since non-rigid registration itself is specialized for local deformation, there is a problem in that deformation with a large translation radius is difficult.

Accordingly, in the present disclosure, a method of using non-rigid registration is applied when performing detailed second alignment after aligning the distorted center with rigid registration.

A general non-rigid registration method is processed slowly through the CPU, but a deep learning-based method is fast by using the GPU.

Accordingly, it is possible to acquire a speed advantage by performing non-rigid registration through a network called VoxelMorph.

This method may show at least 100 times faster speed and higher accuracy than the classic non-rigid registration method for generating a network for performing non-rigid registration.

The proposed rigid registration and non-rigid registration processes have an advantage of minimizing the aforementioned data variance.

Figure 14:
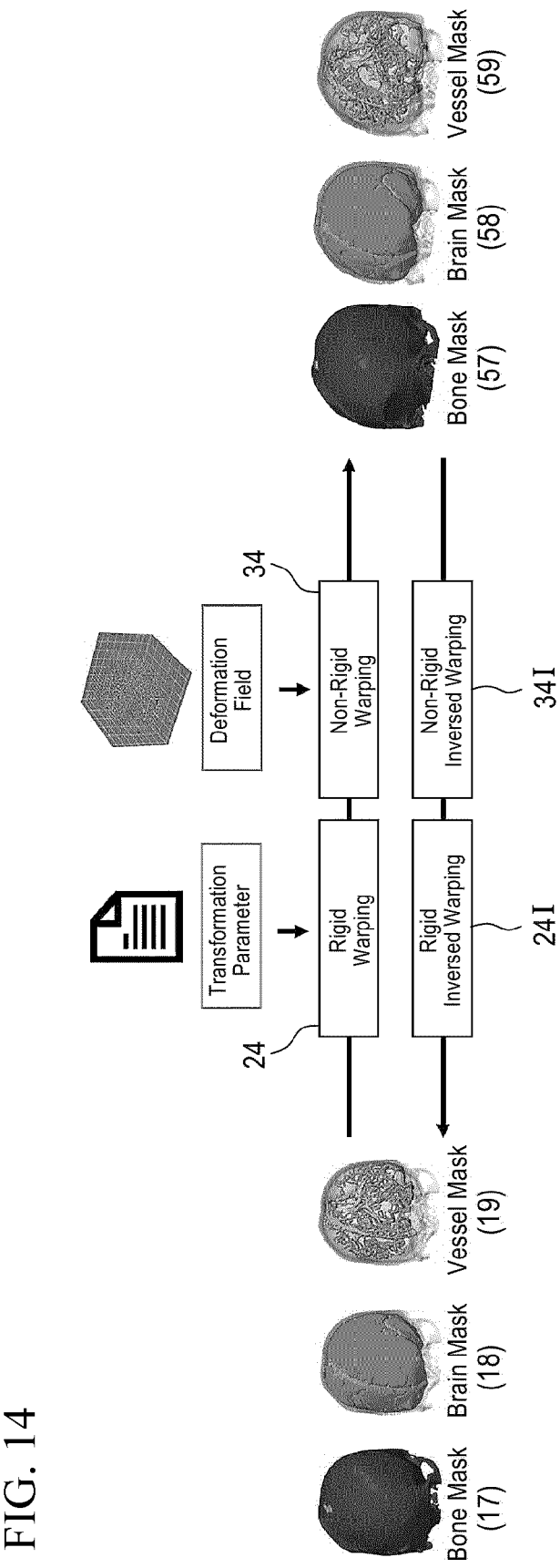
FIG. 14 illustrates an example of using a segment or analysis result in an original CTA image by inversely transforming a result analyzed on rigid/non-rigid registration into a space of the original CTA.

FIG. 14 illustrates an example of using a segment or analysis result in an original CTA image by inversely transforming a result analyzed on rigid/non-rigid registration into a space of the original CTA.

As illustrated in FIG. 14, the method proposed by the present disclosure provides both rigid registration and non-rigid registration results, and an inverse transformation process to the original CTA may also be effective.

When sensitive to a local error according to each characteristic, only linear transformation is applied to use the centrally aligned rigid registration result, and when the region of interest between patients is spatially matched or monitoring is required, a non-rigid registration result may be used.

In addition, the result analyzed on each rigid/non-rigid registration may be inversely transformed into a space of the original CTA to visualize segments or analysis results in the original CTA image.

Referring to FIG. 14, the second aligned brain image N, and the second aligned bone mask 57, brain mask 58, and vessel mask 59 may extract the first aligned brain image R and the first aligned bone mask, brain mask, and vessel mask by inversely transforming and applying (341) the deformation field 36.

Furthermore, the first aligned brain image R and the first aligned bone mask, brain mask, and vessel mask may extract the brain image K, the bone mask 17, the brain mask 18, and the vessel mask 19 by inversely transforming and applying (241) the transformation parameter 26.

Operation of 3D Neurovascular Segmentation Unit

Figure 15:
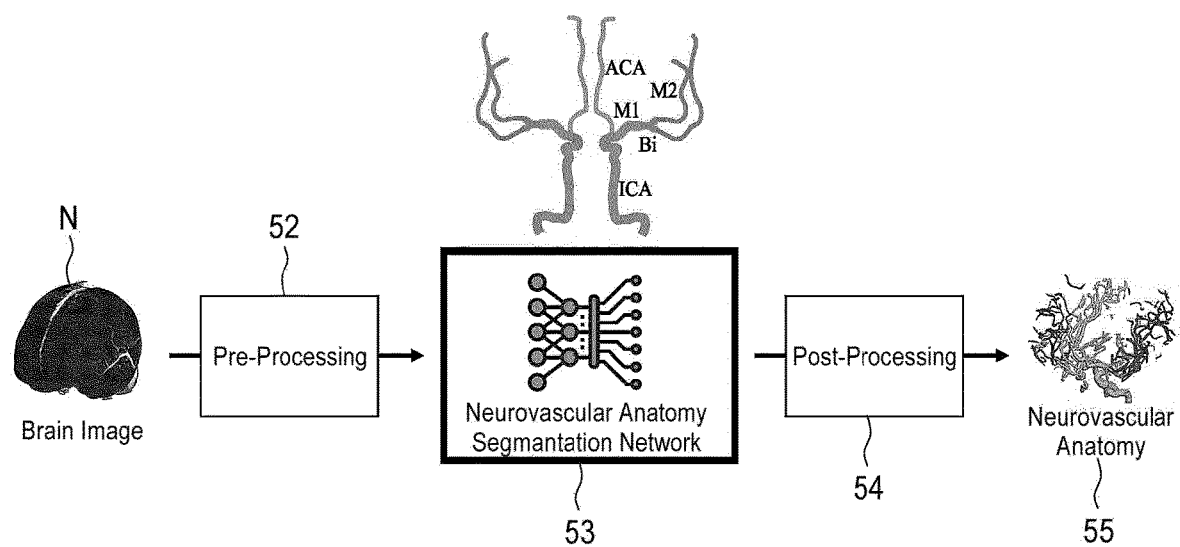
FIG. 15 illustrates an operation of a neurovascular segmentation unit described in FIG. 10 over time.

FIG. 15 illustrates an operation of the neurovascular segmentation unit described in FIG. 10 over time.

Referring to FIG. 15, the non-rigid registration-warped brain image receiving unit 51 receives a second aligned brain image N from the non-rigid registration unit 30.

The segmentation pre-processing unit 52 may perform pre-processing, which is at least one of a HU windowing operation, a normalizing operation, and a patch sampling operation, on the second aligned brain image N.

Here, the pre-processed second aligned brain image passes through the neurovascular anatomy segmentation network 53, and the segmentation post-processing unit 54 performs the post-processing of removing an outlier cluster with respect to the second aligned brain image passing through the neurovascular anatomy segmentation network 53.

The outlier cluster removing operation is an operation of removing the outlier cluster that is not connected but separated on the three dimensions.

In addition, the 3D neurovascular generation unit 54.5 extracts the cerebrovascular map 55 based on the post-processed second aligned brain image.

The neurovascular anatomy extracted from the model may be used to visualize a position in the results of detecting and predicting indications for each vessel, such as large vessel occlusion (LVO) and aneurysm, or to suppress false-positive prediction.

That is, the information provided by the determination unit 60 may further include location information on the cerebrovascular map in which indications are detected and/or predicted, and false-positive related information.

Effects Provided by the Present Disclosure

According to the present disclosure, it is possible to provide a user with artificial intelligence-based devices and methods capable of transforming raw CT images in consistent directions and sizes when the raw CT images have been input.

According to the present disclosure, it is possible to provide a user with a device and a method capable of minimizing diversity caused by the size and shape, imaging direction, etc. of the patient's skull by applying a process of transforming any raw CT image in a consistent direction and size when the raw CT image has been input.

According to the present disclosure, in a series of processes of taking CT angiography in medical data, since protocols such as an image-taking angle, an image-taking area, a patient orientation, a slice thickness, a slice interval, etc. vary for each situation depending on a vendor of each hospital and habits of the tomographer, it is possible to solve a problem that data have geometrically various variances.

In general, when checking the slices of an axial axis of each data, the anatomical patterns and aspects appearing in each slice are different each time, and in the process of analyzing medical data, data variance appearing according to various imaging protocols is a major cause of lowering accuracy, but the geometrical registration process proposed by the present disclosure may minimize these data variances.

In addition, the method proposed by the present disclosure provides both rigid registration and non-rigid registration results, and an inverse transformation process to the original CTA may also be effective.

According to the present disclosure, when sensitive to a local error according to each characteristic, only linear transformation is applied to use the centrally aligned rigid registration result, and when the region of interest between patients is spatially matched or monitoring is required, a non-rigid registration result may be used.

In addition, the result analyzed on each rigid/non-rigid registration may be inversely transformed into a space of the original CTA to visualize segments or analysis results in the original CTA image.

In addition, in the present disclosure, if specific brain compartments M1 to M6 are used for classification in the original CT image, non-rigid registration is performed, and then standard compartment (M1 to M6) masks of the corresponding space may be applied to be extracted and analyzed. Similarly, inverse transformation to the original CT space may be performed and indicated on the original CT image.

In addition, in the present disclosure, when anatomical information of each vessel and brain region, such as neurovascular anatomy and brain anatomy, is required, a specific region may be distinguished after registration through non-rigid registration. Similarly, inverse transformation to the original CT space may be performed and indicated even on the original CT image.

In addition, in the present disclosure, when monitoring such as aneurysm and tumor is required, the progress of lesions may be shown by matching the images of the same patient taken at different times by performing non-rigid registration.

A technical object to be achieved in the present disclosure is not limited to the aforementioned effects, and another not-mentioned effect will be obviously understood by those skilled in the art from the description below.

The above-described exemplary embodiments of the present disclosure may be implemented through various methods. For example, the exemplary embodiments of the present disclosure may be implemented by a hardware, a firmware, a software, or a combination thereof.

When the exemplary embodiment is implemented by the hardware, the method according to the exemplary embodiment of the present disclosure may be implemented by one or more application specific integrated circuits (ASICs), digital signal processors (DSPs), digital signal processing devices (DSPDs), programmable logic devices (PLDs), field programmable gate arrays (FPGAs), a processor, a controller, a microcontroller, or a microprocessor.

When the exemplary embodiment is implemented by the firmware or the software, the method according to the exemplary embodiment of the present disclosure may be implemented by a module, a procedure, or a function which performs a function or operations described above. The software code is stored in the memory unit to be driven by the processor. The memory unit is located inside or outside the processor and may exchange data with the processor, by various known units.

As described above, the detailed description of the preferred exemplary embodiments of the disclosed present disclosure is provided such that those skilled in the art implement and carry out the present disclosure. While the present disclosure has been described with reference to the preferred exemplary embodiments, it will be understood by those skilled in the art that various changes and modifications of the present disclosure may be made without departing from the scope of the present disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the spirit and essential feature of the present disclosure. Therefore, the above-detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the exemplary embodiment or may be included as new claims by correction after application.

What is claimed is:

1. An information providing method comprising:
   a first step of receiving a CT image by a head segmentation unit;
   a second step of predicting, by the head segmentation unit, a bone mask of a skull, a brain mask of a brain, and a brain-related vessel mask by passing the CT image through a head segmentation network capable of separating the skull and the brain;
   a third step of extracting, by the head segmentation unit, a brain image including only a brain region from the CT image by combining the predicted brain mask and vessel mask;
   a fourth step of receiving, by a rigid registration unit, standardized template data from an atlas unit and receiving the brain image from the head segmentation unit by fusing characteristics of specific samples to be used as a reference for aligning a plurality of data into a common space;
   a fifth step of performing, by the rigid registration unit, rigid registration and affine registration between the template data and the brain image to acquire a transformation parameter;
   a sixth step of applying, by the rigid registration unit, rigid warping to the brain image based on the transformation parameter to acquire a first aligned brain image aligned by a linear transformation;
   a seventh step of extracting, by a non-rigid registration unit, a deformation field which is a translation vector for each 3D voxel by inputting a 3D volume of the template data and a 3D volume of the first aligned brain image to a pre-learned non-rigid registration network;
   an eighth step of acquiring, by the non-rigid registration unit, a second aligned brain image more accurately registered to the actual brain than a result of the sixth step by performing non-rigid warping that applies grid interpolation in units of voxels to the first aligned brain image based on the deformation field;
   a ninth step of extracting, by a neurovascular segmentation unit, a cerebrovascular map from the second aligned brain image by passing the second aligned brain image through a neurovascular anatomy segmentation network; and
   a tenth step of providing, by a determination unit, brain-related information based on the cerebrovascular map,
   wherein the second step comprises
   a 2-1 step of performing pre-processing which is at least one of a resizing operation, a HU windowing operation, and a normalizing operation with respect to the CT image;
   a 2-2 step of passing the pre-processed CT image through the head segmentation network;

a 2-3 step of performing post-processing, which is at least one of a brain VOI crop operation and an outlier cluster removing operation with respect to the CT image passing through the head segmentation network; and a 2-4 step of predicting the bone mask, the brain mask, and the vessel mask based on the post-processed CT image.

2. The information providing method of claim 1, wherein in the 2-1 step, the resizing operation is an operation of reducing and/or enlarging an image to a size required by the head segmentation network, the HU windowing operation is an operation of setting upper and lower limits of a Hounsfield unit (HU), and the normalizing operation is an operation of determining a HU Level from the set lower limit to the upper limit, and mapping the level at a determined interval, and in the 2-3 step, the brain VOI crop operation is an operation of resizing after removing a region other than a volume region of interest for the brain, and the outlier cluster removing operation is an operation of removing the outlier cluster that is not connected but separated on three dimensions.

3. The information providing method of claim 1, wherein the standardized template data of the atlas unit is generated by aligning the specific sample data in a center so that anatomical patterns or characteristics are preserved and synthesizing the specific sample data after registration according to a predetermined level.

4. The information providing method of claim 1, wherein the rigid warping based on the transformation parameter applies the linear transformations including translation, rotation, and scale transformations so that the brain image is deformed while maintaining an original ratio without distortion.

5. The information providing method of claim 4, wherein in the non-rigid warping based on the deformation field, alignment is performed to make a shape more consistent with the actual brain by performing detailed secondary alignment on the first aligned brain image based on the transformation parameter by applying the grid interpolation in units of voxels.

6. The information providing method of claim 1, wherein in the ninth step, the cerebrovascular map is extracted by dividing an anatomical structure of an artery, and in the tenth step, the information includes data for dividing indications according to a vascular structure.

7. The information providing method of claim 6, wherein the indications according to the vascular structure include large vessel occlusion (LVO) and aneurysm, and in the tenth step, the information includes location information on the cerebrovascular map in which the indications are detected and/or predicted, and false-positive related information.

8. A device comprising:

a head segmentation unit configured to receive a CT image, predict a bone mask of a skull, a brain mask of a brain, and a brain-related vessel mask by passing the CT image through a head segmentation network capable of separating the skull and the brain, and extract a brain image including only a brain region from the CT image by combining the predicted brain mask and vessel mask;

a rigid registration unit configured to receive standardized template data from an atlas unit and receive the brain image from the head segmentation unit by fusing characteristics of specific samples to be used as a reference for aligning a plurality of data into a common space, perform rigid registration and affine registration between the template data and the brain image to acquire a transformation parameter, and apply rigid warping to the brain image based on the transformation parameter to acquire a first aligned brain image aligned by a linear transformation;

a non-rigid registration unit configured to extract a deformation field which is a translation vector for each 3D voxel by inputting a 3D volume of the template data and a 3D volume of the first aligned brain image to a pre-learned non-rigid registration network, and acquire a second aligned brain image more accurately registered to the actual brain than a result of the rigid registration unit by performing non-rigid warping that applies grid interpolation in units of voxels to the first aligned brain image based on the deformation field;

a neurovascular segmentation unit configured to extract a cerebrovascular map from the second aligned brain image by passing the second aligned brain image through a neurovascular anatomy segmentation network; and a determination unit configured to provide brain-related information based on the cerebrovascular map, wherein the head segmentation unit is configured to perform pre-processing which is at least one of a resizing operation, a HU windowing operation, and a normalizing operation, with respect to the CT image;

pass the pre-processed CT image through the head segmentation network;

perform post-processing, which is at least one of a brain VOI crop operation and an outlier cluster removing operation with respect to the CT image passing through the head segmentation network; and predict the bone mask, the brain mask, and the vessel mask based on the post-processed CT image.

9. The device of claim 8, wherein the resizing operation is an operation of reducing and/or enlarging an image to a size required by the head segmentation network, the HU windowing operation is an operation of setting upper and lower limits of a Hounsfield unit (HU), the normalizing operation is an operation of determining a HU Level from the set lower limit to the upper limit, and mapping the level at a determined interval, the brain VOI crop operation is an operation of resizing after removing a region other than a volume region of interest for the brain, and the outlier cluster removing operation is an operation of removing the outlier cluster that is not connected but separated on three dimensions.

10. The device of claim 8, wherein the standardized template data of the atlas unit is generated by aligning the specific sample data in a center so that anatomical patterns or characteristics are preserved and synthesizing the specific sample data after registration according to a predetermined level, rigid warping based on the transformation parameter applies the linear transformations including translation, rotation, and scale transformations so that the brain image is deformed while maintaining an original ratio without distortion, and in the non-rigid warping based on the deformation field, alignment is performed to make a shape more consistent with the actual brain by performing detailed secondary alignment on the first aligned brain image based on the transformation parameter by applying the grid interpolation in units of voxels.

11. The device of claim 8, wherein the cerebrovascular map is extracted by dividing an anatomical structure of an artery, the information includes data for dividing indications according to a vascular structure, the indications according to the vascular structure include large vessel occlusion (LVO) and aneurysm, and the information provided by the determination unit includes location information on the cerebrovascular map in which the indications are detected and/or predicted, and false-positive related information.

* * * * *